United States Patent
Kesten et al.

(10) Patent No.: US 10,064,555 B2
(45) Date of Patent: Sep. 4, 2018

(54) ILLUMINATING GUIDEWIRE WITH OPTICAL SENSING

(71) Applicant: Acclarent, Inc., Menlo Park, CA (US)

(72) Inventors: Randy J. Kesten, Mountain View, CA (US); Scott O. Chamness, Menlo Park, CA (US); Thomas R. Jenkins, Alameda, CA (US)

(73) Assignee: Acclarent, Inc., Irvine, CA (US)

( * ) Notice: Subject to any disclaimer, the term of this patent is extended or adjusted under 35 U.S.C. 154(b) by 160 days.

(21) Appl. No.: 14/824,377

(22) Filed: Aug. 12, 2015

(65) Prior Publication Data
US 2016/0287083 A1 Oct. 6, 2016

Related U.S. Application Data

(60) Provisional application No. 62/140,643, filed on Mar. 31, 2015.

(51) Int. Cl.
*A61B 5/00* (2006.01)
*A61B 1/07* (2006.01)
(Continued)

(52) U.S. Cl.
CPC .............. *A61B 5/0084* (2013.01); *A61B 1/01* (2013.01); *A61B 1/07* (2013.01); *A61B 1/233* (2013.01);
(Continued)

(58) Field of Classification Search
CPC ......... A61B 5/00; A61B 5/055; A61B 5/4869; A61B 5/7246; A61B 5/7264; A61B 5/7275; A61B 6/482; G01R 33/48
See application file for complete search history.

(56) References Cited

U.S. PATENT DOCUMENTS 5,383,467 A * 1/1995 Auer .................... A61B 5/0084
600/342
5,951,482 A * 9/1999 Winston ............... A61B 5/0084
356/477
(Continued)

FOREIGN PATENT DOCUMENTS

EP 1071370 1/2001
EP 2441489 4/2012

OTHER PUBLICATIONS

U.S. Appl. No. 62/140,643, filed Mar. 31, 2015.
International Search Report and Written Opinion dated Jun. 10, 2016 re Application No. PCT/US2016/024719.

*Primary Examiner* — Amanda Patton
(74) *Attorney, Agent, or Firm* — Frost Brown Todd LLC

(57) ABSTRACT

A guide member system includes a guide member, a light source, and a detector. The guide member comprises at least one illumination fiber. The at least one illumination fiber distally transmits the light projected by the light source from the proximal end of the guide member to the distal end of the guide member. The distal end of the guide member is projects the distally transmitted light. The distal end of the guide member receives light projected from the distal end of the guide member and reflected back toward the distal end of the guide member. The at least one illumination fiber proximally transmits the reflected light from the distal end of the guide member to the proximal end of the guide member. The proximal end of the guide member projects the proximally transmitted light toward the detector. The detector detects the proximally transmitted light.

20 Claims, 22 Drawing Sheets

(51) Int. Cl.
  *A61B 1/233* (2006.01)
  *A61B 1/01* (2006.01)
  *A61B 5/06* (2006.01)
  *A61B 5/103* (2006.01)
  *A61M 25/09* (2006.01)
  *A61B 1/00* (2006.01)
  *A61B 5/107* (2006.01)
  *A61M 25/01* (2006.01)
  *A61M 25/10* (2013.01)
  *A61B 17/00* (2006.01)
  *A61B 90/30* (2016.01)
  *A61M 25/00* (2006.01)
  *A61M 29/02* (2006.01)
  *A61M 25/06* (2006.01)

(52) U.S. Cl.
  CPC .............. *A61B 5/065* (2013.01); *A61B 5/486* (2013.01); *A61B 5/6819* (2013.01); *A61B 5/6851* (2013.01); *A61B 5/6853* (2013.01); *A61M 25/09* (2013.01); *A61B 1/00183* (2013.01); *A61B 5/1032* (2013.01); *A61B 5/1076* (2013.01); *A61B 2017/00057* (2013.01); *A61B 2090/306* (2016.02); *A61M 25/0041* (2013.01); *A61M 25/0105* (2013.01); *A61M 25/10* (2013.01); *A61M 25/10182* (2013.11); *A61M 29/02* (2013.01); *A61M 2025/0681* (2013.01); *A61M 2025/0915* (2013.01); *A61M 2025/09083* (2013.01); *A61M 2025/09175* (2013.01); *A61M 2210/0618* (2013.01); *A61M 2210/0681* (2013.01)

(56) References Cited

U.S. PATENT DOCUMENTS

| | | |
|---|---|---|
| 7,630,676 B2 | 12/2009 | Pirwitz |
| 9,155,492 B2 | 10/2015 | Jenkins et al. |
| 2008/0183128 A1 | 7/2008 | Morriss et al. |
| 2010/0030031 A1 | 2/2010 | Goldfarb et al. |
| 2011/0004057 A1 | 1/2011 | Goldfarb et al. |
| 2014/0074141 A1 | 3/2014 | Johnson et al. |
| 2014/0275775 A1 | 9/2014 | Jones et al. |

* cited by examiner

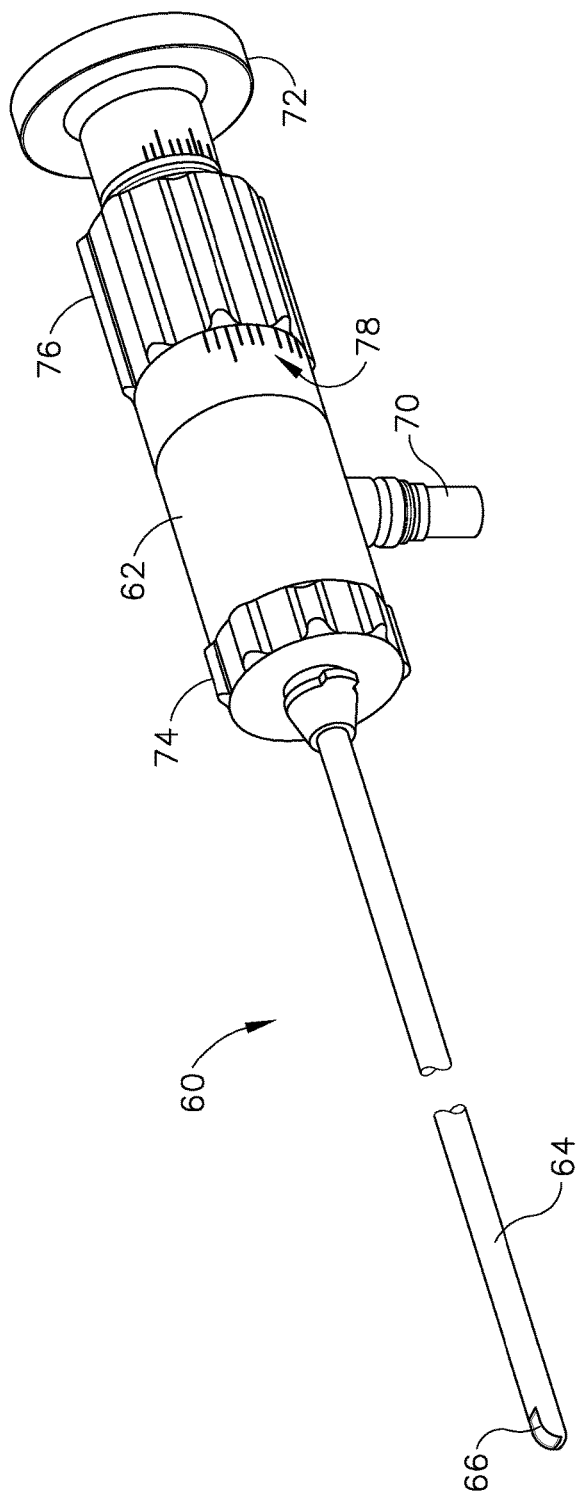
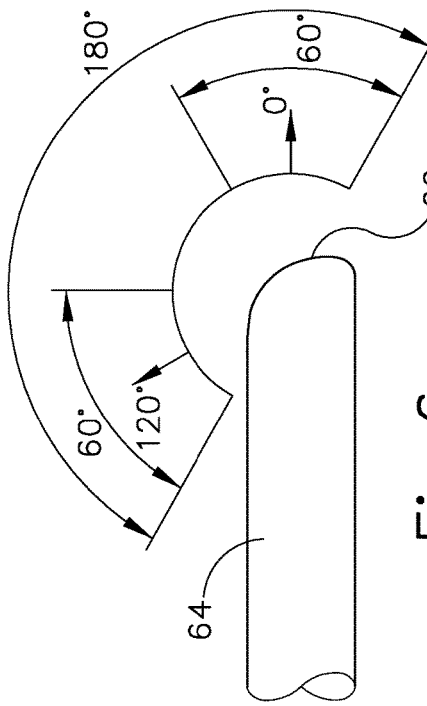
Fig.5
Fig.6

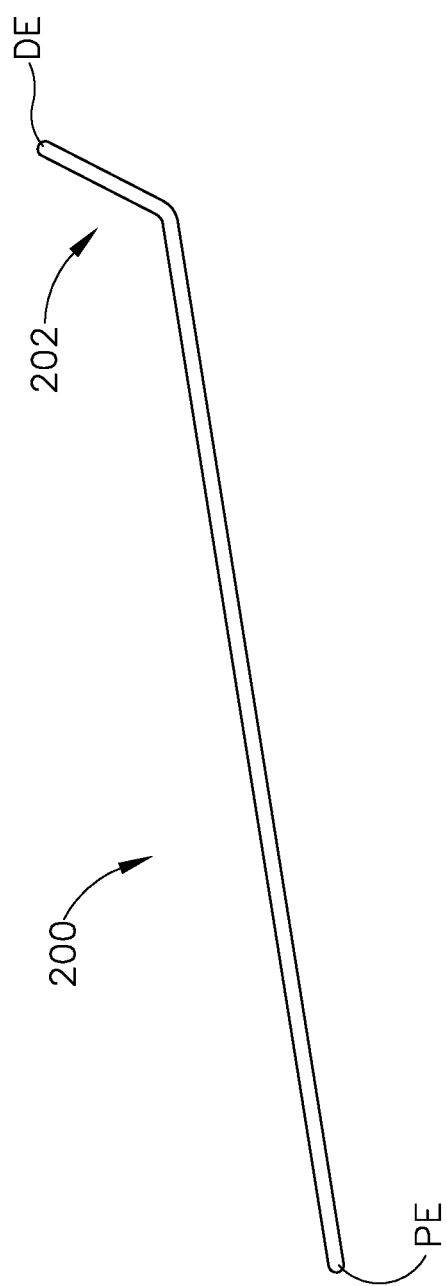

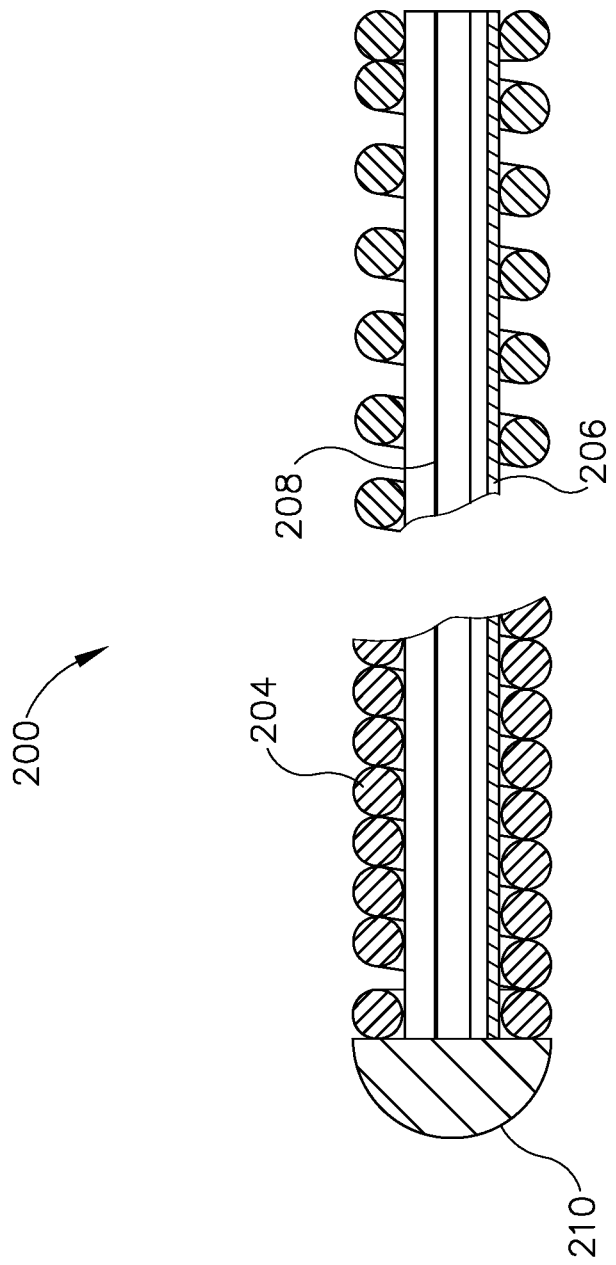

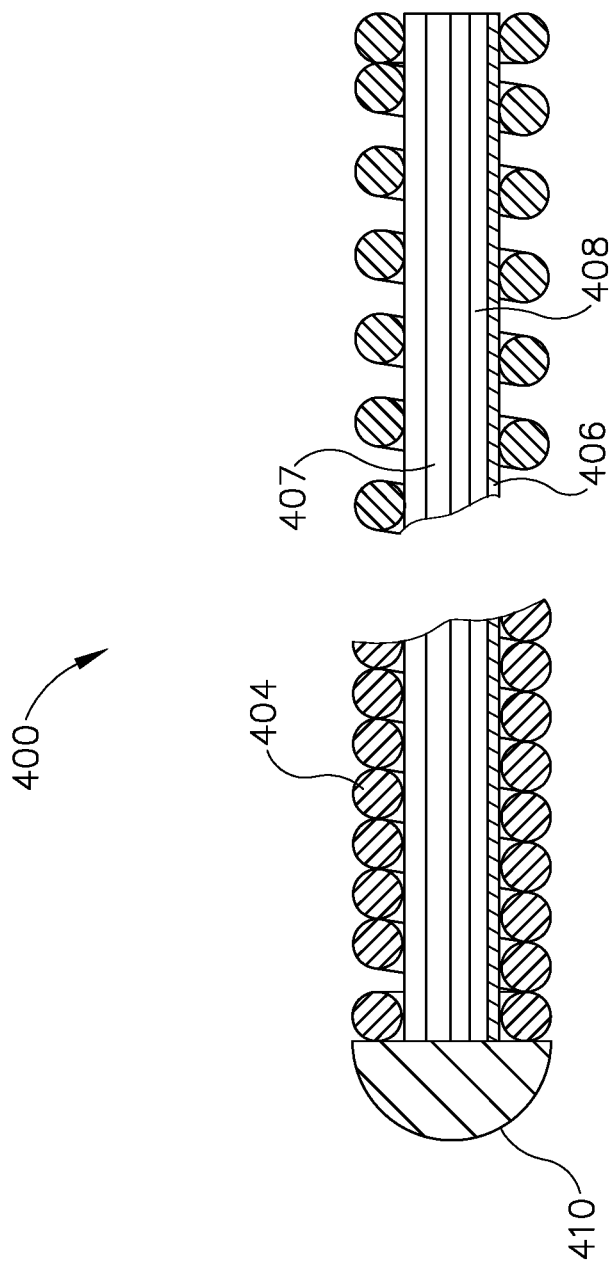

ILLUMINATING GUIDEWIRE WITH OPTICAL SENSING

PRIORITY

This application claims priority to U.S. Provisional Patent App. No. 62/140,643, entitled "Illuminating Guidewire with Optical Sensing," filed Mar. 31, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5 depicts a perspective view of an exemplary endoscope suitable for use with the dilation catheter system of FIG. 1;

FIG. 6 depicts a side elevational view of the distal end of the endoscope of FIG. 5, showing an exemplary range of viewing angles;

FIG. 8 depicts a perspective view of an exemplary alternative illuminating guidewire suitable for use with the dilation catheter system of FIG. 1;

FIG. 9 depicts cross-sectional side view of the distal end of the illuminating guidewire of FIG. 8;

FIG. 11 depicts an exemplary detailed cross-sectional side view of the distal end of an exemplary alternative illuminating guidewire suitable for use with the dilation catheter system of FIG. 1;

Figure 1:
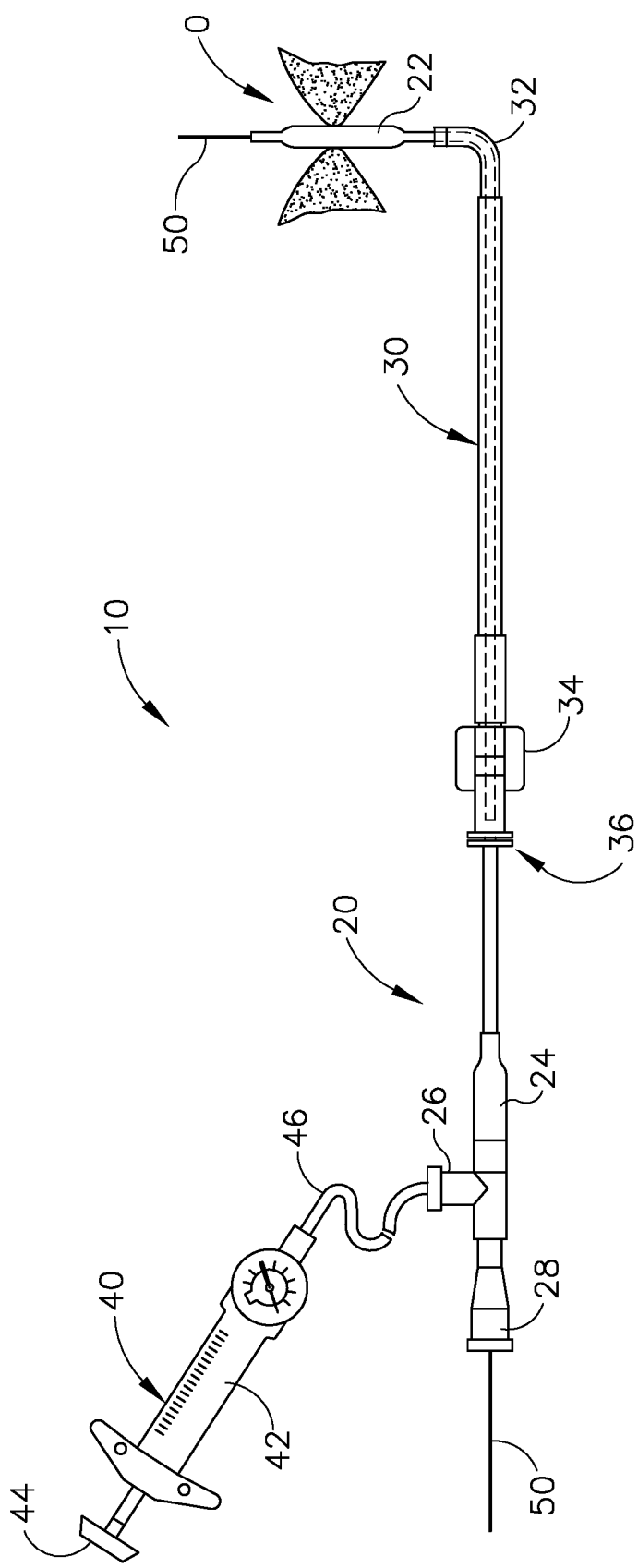
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2A:
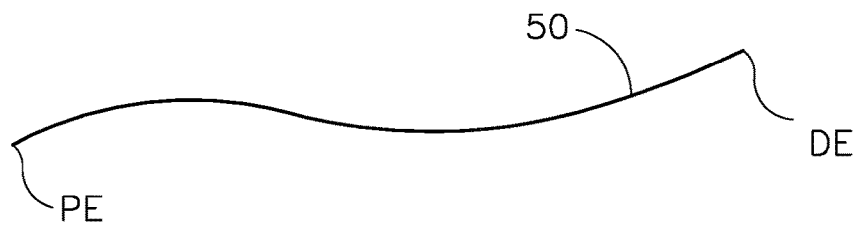
FIG. 2A depicts a side elevational view of an exemplary illuminating guidewire of the dilation catheter system of FIG. 1.
Figure 2B:
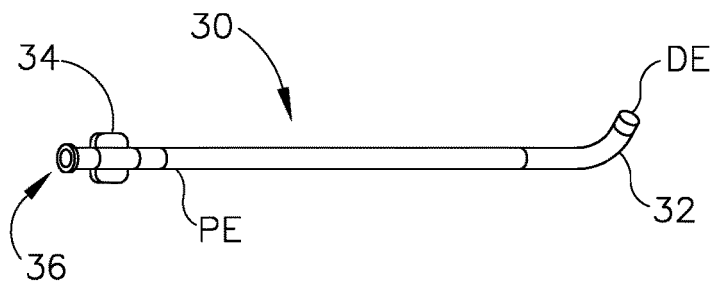
FIG. 2B depicts a side elevational view of an exemplary guide catheter of the dilation catheter system of FIG. 1.
Figure 2C:
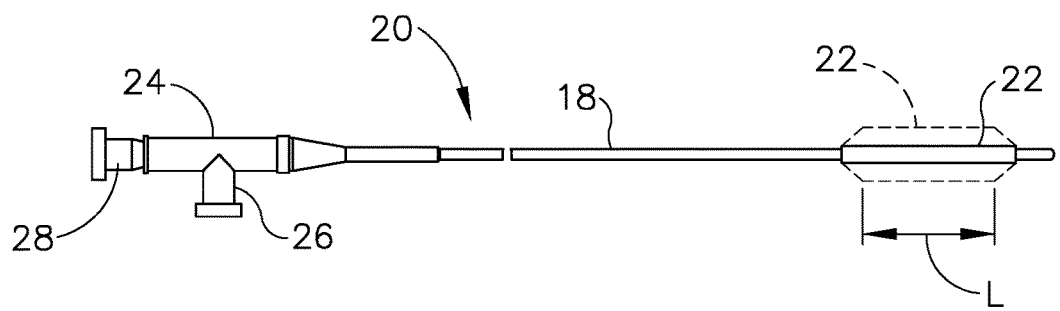
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, now U.S. Pat. No. 9,962,530, issued May 8, 2018, the disclosure of which is incorporated by reference herein.

Figure 3:
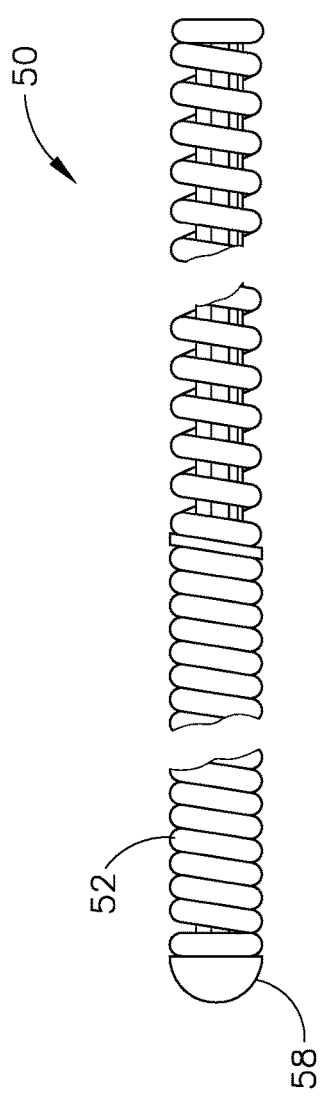
FIG. 3 depicts a detailed side elevational view of the illuminating guide wire of FIG. 2A.
Figure 4:
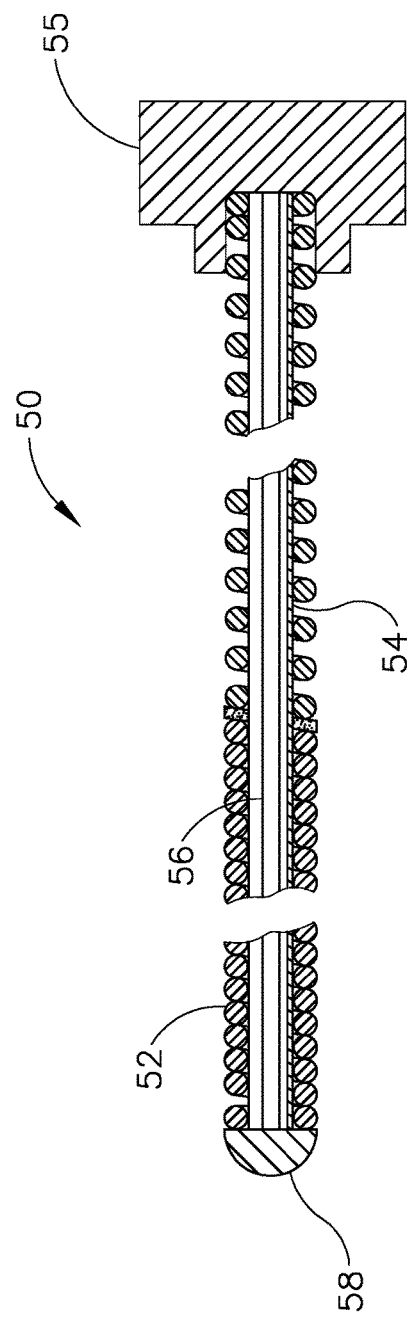
FIG. 4 depicts a detailed side cross-sectional view of the illuminating guidewire of FIG. 2A.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Method for Dilating the Ostium of a Maxillary Sinus FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
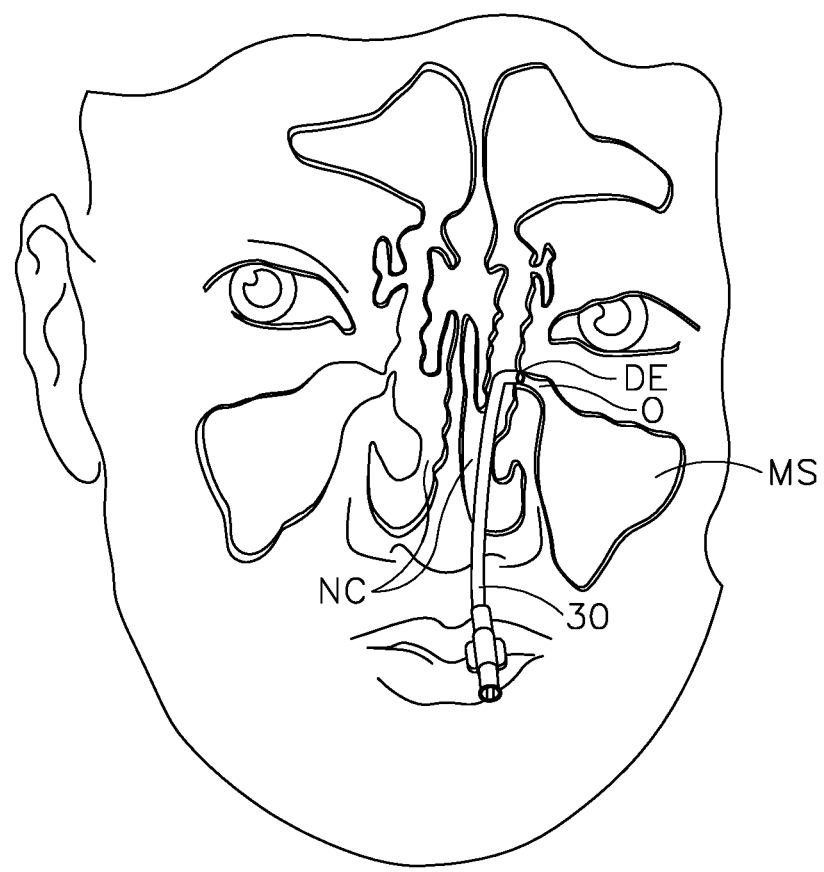
FIG. 7A depicts a front view of the guide catheter of FIG. 2B positioned adjacent an ostium of the maxillary sinus.
Figure 7C:
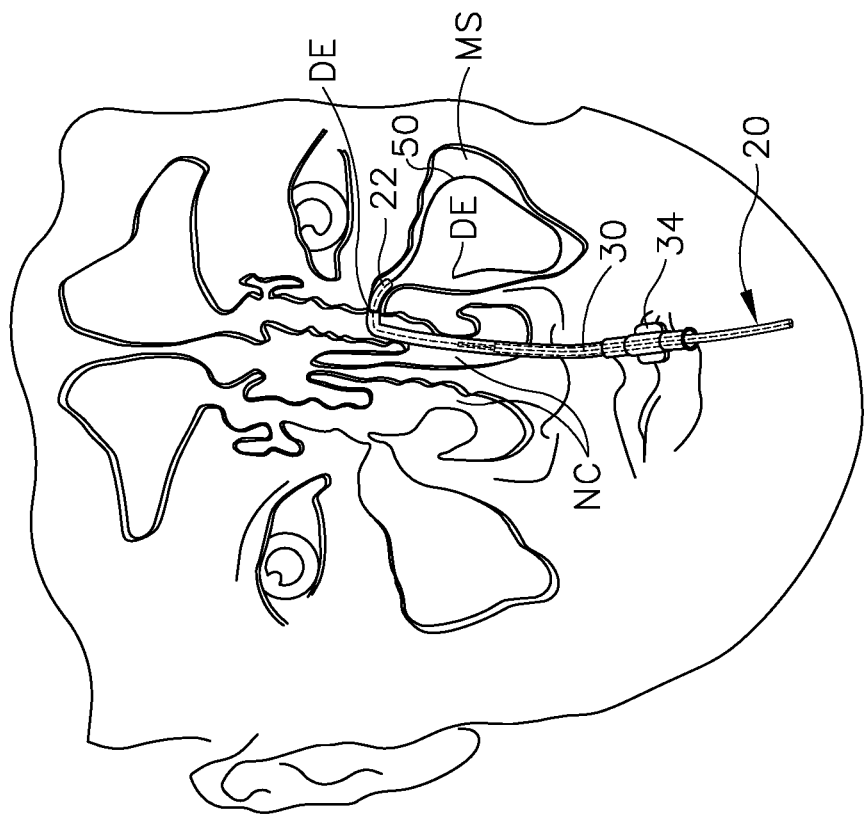
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 7B:
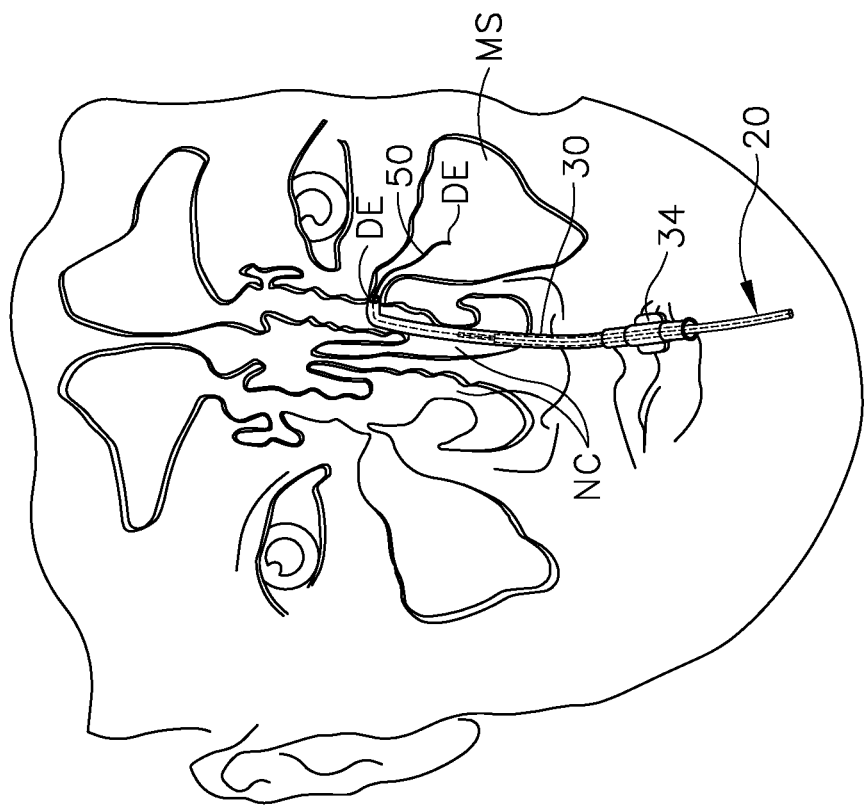
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7E:
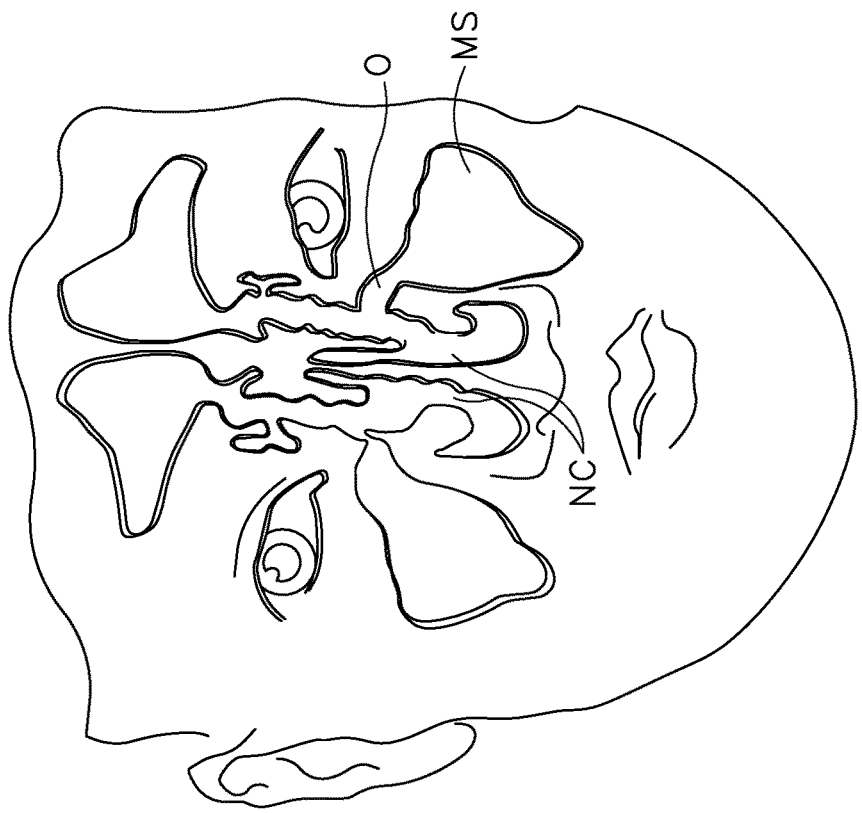
FIG. 7E depicts a front view of an ostium of the maxillary sinus, with the ostium having been enlarged by inflation of the balloon of FIG. 7D.
Figure 7D:
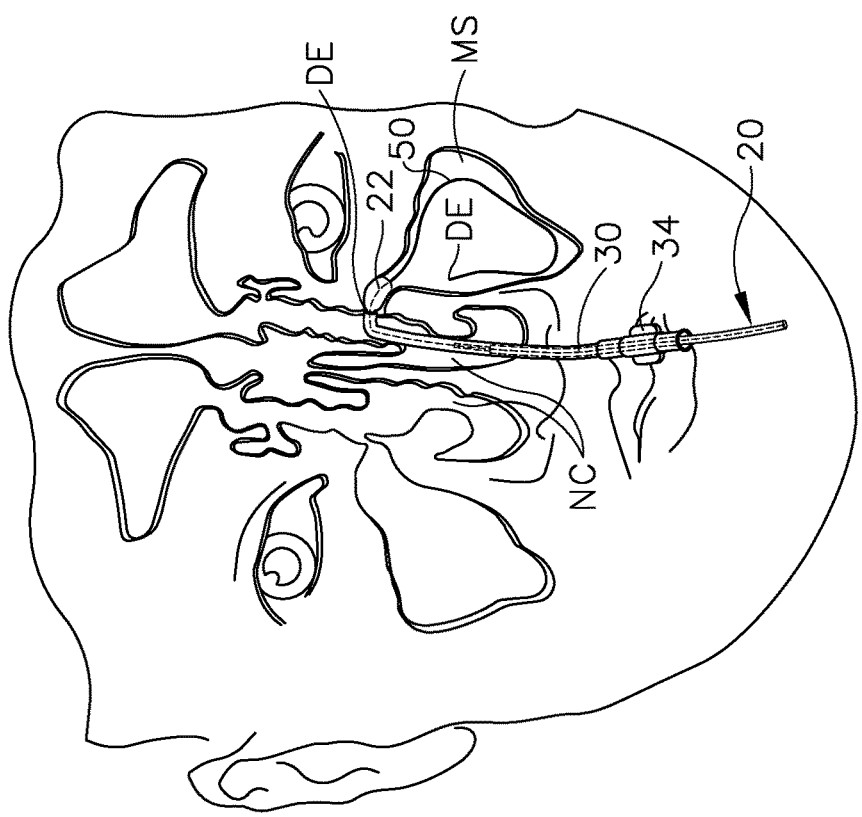
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (0). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pat. Pub. No. 2008/0183128, entitled "Methods, Devices and Systems for Treatment and/or Diagnosis of Disorders of the Ear, Nose and Throat," published on Jul. 31, 2008, the disclosure of which is incorporated by reference herein. An example of an irrigation catheter that may be fed through guide catheter (30) to reach the irrigation site after removal of dilation catheter (20) is the Relieva Vortex®. Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra®. Sinus Irrigation Catheter by Acclarent, Inc. of Menlo Park, Calif. Of course, irrigation may be provided in the absence of a dilation procedure; and a dilation procedure may be completed without also including irrigation.

IV. Exemplary Illuminating Guidewire Systems

In some versions of dilation catheter system (10) it may be desirable to provide illuminating guidewire (50) with features that allow an operator to receive information concerning a position of guidewire (50) within the patient even when guidewire (50) is not visible via endoscope (60); and when guidewire (50) is not yet in a position to provide transillumination that is visible from outside the patient. For instance, as will be described below, some versions of guidewire (50) may be provided with light transmitting features that are configured to transmit light distally (i.e., from the proximal end (PE) of guidewire (50) to the distal end (DE) of guidewire (50)) and proximally (i.e., from the distal end (DE) of guidewire (50) to the proximal end (PE) of guidewire (50)) along the length of guidewire (50). As will be described in more detail below, such bi-directional transmission of light may be used to indicate and/or detect a position of guidewire (50) within a patient. Various examples of such guidewires will be described in greater detail below; while other examples will be apparent to those of ordinary skill in the art in view of the teachings herein. While the following examples are provided in the context of dilating the ostium (O) of the maxillary sinus (MS) it should be understood that the same examples may be readily applied to the context of dilating the Eustachian tube, other ostia of paranasal sinuses, the frontal recess, and/or other anatomical passageways associated with the ear, nose, and throat.

A. Exemplary Illuminating Guidewire System

FIG. 8 shows an exemplary flexible-illuminating guidewire (200) that may be readily incorporated into dilation catheter system (10) in place of guidewire (50). Guidewire (200) of the present example includes a preformed bent distal portion (202) at its distal end (DE). In particular, bent distal portion (DE) defines an obtuse angle. In some other versions, bent distal portion has a curved configuration rather than an angular configuration. In still other versions, distal portion (DE) is simply straight, such that there is no curve or angular bend. As will be discussed in more detail below, bent distal portion (202) is operable transmit light over a selected region as the result of rotating guidewire (200) about the longitudinal axis of guidewire (200).

As shown in FIG. 9, guidewire (200) of the present example comprises a coil (204) positioned about a core wire (206). An illumination fiber (208) extends along the interior of core wire (206), alongside core wire (206), and terminates in an atraumatic lens (210). Although illumination fiber (208) of the present example comprises a single optical fiber, illumination fiber (208) may be supplemented with additional optical fibers as will be described in more detail below. Lens (210) is configured to project light when illumination fiber (208) is illuminated by a light source, such that illumination fiber (208) transmits light from the light source to the lens (210). As will be discussed in more detail below, lens (210) is further configured to receive and transmit light to illumination fiber (208) when that light is reflected from beyond the distal end (DE) of guidewire (200).

In some versions, the distal end (DE) of guidewire (200) is more flexible than the proximal end (PE) of guidewire (200). Guidewire (200) has a length enabling the distal end (DE) of guidewire (200) to be positioned distal to dilator (22) while the proximal end (PE) of guidewire (200) is positioned proximal to grip (24). Guidewire (200) may include indicia along at least part of its length (e.g., the proximal portion) to provide the operator with visual feedback indicating the depth of insertion of guidewire (200) relative to dilation catheter (20). By way of example only, guidewire (200) may be configured and operable in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (200) is configured similar to the Relieva Luma Sentry™ Sinus Illumination System by Acclarent, Inc. of Menlo Park, Calif. Other suitable forms that guidewire (200) may take will be apparent to those of ordinary skill in the art in view of the teachings herein.

FIGS. 10A-10F show an exemplary illuminating system (300) and an exemplary method for using illuminating system (300) with guidewire (200) to access the maxillary sinus (MS) of a patient. Illuminating system (300) of the present example comprises a conventional light source (302), a conventional beam splitter (304), and a conventional light detector (306). Light source (302) may comprise any suitable kind of light source (302) and may include various components, including but not limited to a laser, a beam collimator, focusing optics, etc. Light source (302) may be operable to communicate any suitable kind of light, including but not limited to white/visible light, near-infrared light, infrared light, etc. Beam splitter (304) is operable to reflect light from light source (302) in a first direction along a reflected light axis; and transmit light in a second direction along the same axis. Light detector (306) is configured to receive light that is transmitted through beam splitter (304) in the second direction along the reflected light axis. Light detector (306) includes a sensor that is operable to generate electrical signals based on light received by the sensor.

Light detector (306) (and/or one or more components that are coupled with light detector (306)) may further include hardware that is configured to process those generated electrical signals and generate some kind of output that provides feedback to the operator relating to the light received by light detector (306). Such feedback may include audible feedback (e.g., an audible tone, a voice providing spoken words, etc.), visual feedback (e.g., a selectively illuminating LED, a graphical interface providing graphic and/or textual feedback, etc.), and/or tactile feedback (e.g., a feature providing a vibration through a handpiece associated with guide catheter (30), etc.). Various suitable forms that light source (302), beam splitter (304), and light detector (306) (and associated components) may take will be apparent to those of ordinary skill in the art in view of the teachings herein. Similarly, various suitable forms that operator feedback may take will be apparent to those of ordinary skill in the art in view of the teachings herein. In some instances, it may be desirable to configure detector (306) such that detector (306) is operable to "subtract" any unwanted light from light scattering, reflection, or other optical phenomena so as to improve upon the information indicated by detector (306). Various suitable ways in which such subtraction may be provided will be apparent to those of ordinary skill in the art in view of the teachings herein.

Figure 10A:
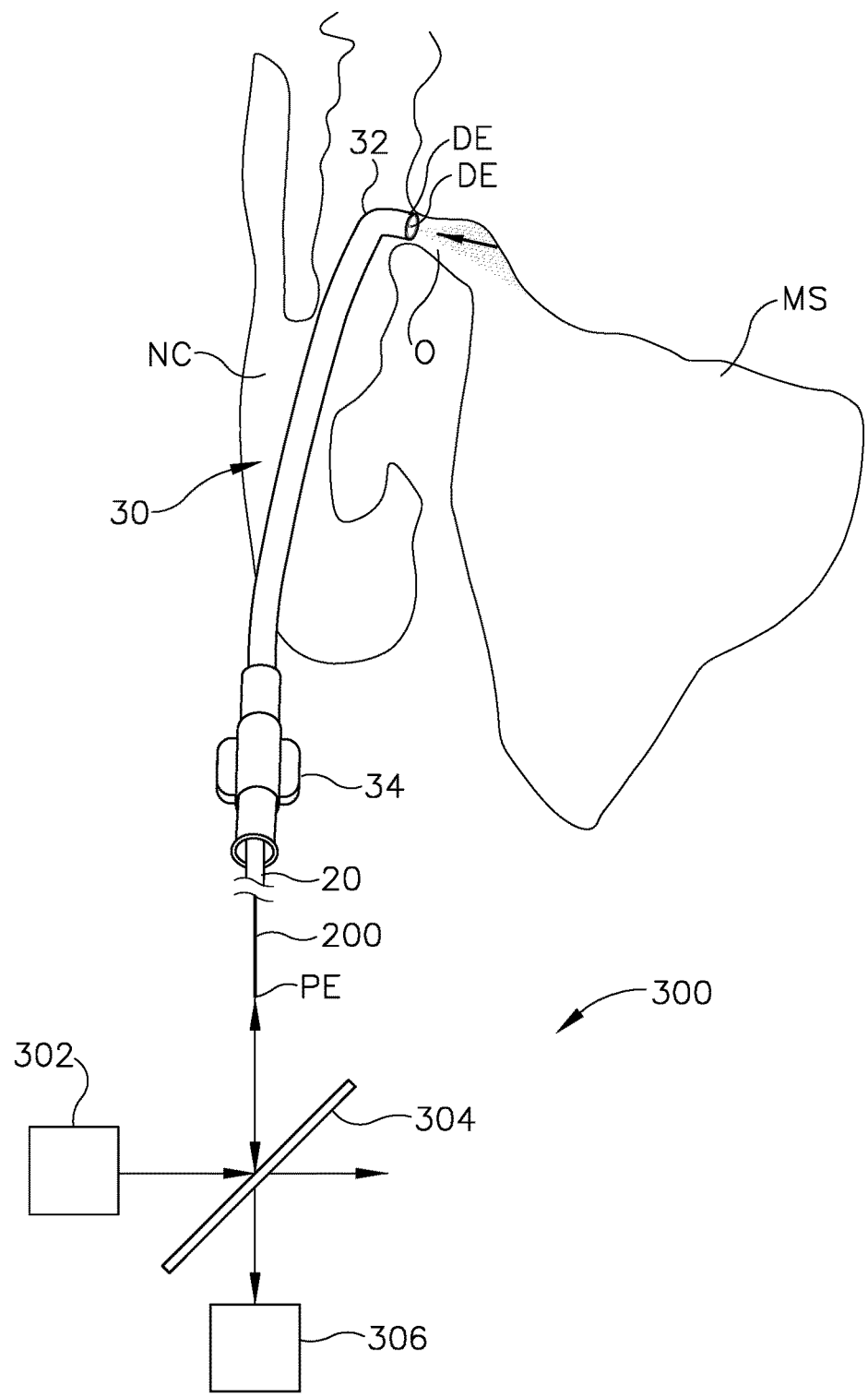
FIG. 10A depicts a front view of the guide catheter of FIG. 2B positioned adjacent an ostium of the maxillary sinus, with the dilation catheter of FIG. 2C and the illuminating guidewire of FIG. 8 positioned therein, and with the illuminating guidewire projecting light through the ostium of the maxillary sinus.

In an exemplary procedure, guide catheter (30) may be inserted transnasally and advanced through the nasal cavity (NC) to a position within or near the ostium (O) of the maxillary sinus (MO) as shown in FIG. 10A. At this stage, the distal end (DE) of guidewire (200) may be positioned adjacent the distal end (DE) of guide catheter (30). At the same time, light source (302) projects light toward beam splitter (304). Beam splitter (304) redirects a portion of the light to project distally through illumination fiber (208) of guidewire (200). This light is transmitted through illumination fiber (208) and is emitted from the distal end (DE) of guidewire (200) via lens (210). This emitted light can serve as a source of transilluminating light operable to indicate a position of the distal end (DE) of guidewire (200) by visualization through the anatomical structure(s) that surrounds the distal end (DE) of guidewire (200). Further, the anatomical structure(s) that surrounds the distal end (DE) of guidewire (200) may reflect at least a portion of this emitted light back toward the distal end (DE) of guidewire (200). This reflected light enters illumination fiber (208) via lens (210). The reflected light is then transmitted proximally through illumination fiber (208) and is emitted from the proximal end (PE) of guidewire (200). This light emitted from the proximal end (PE) of guidewire (200) is then transmitted through beam splitter (304) toward detector (306). Detector (306) is then operable to determine and/or indicate the presence and characteristics of reflected light to thereby determine and/or indicate the presence of anatomical structure(s) that are distal to distal end (DE) of guidewire (200). As noted above, based on the detected light that is reflected back from anatomical structure(s) that are distal to distal end (DE) of guidewire (200), detector (306) and/or components that are coupled with detector (306) may further provide real-time feedback to the operator concerning the position of guidewire (200) and/or the anatomical structure(s) that are distal to distal end (DE) of guidewire (200).

Figure 10B:
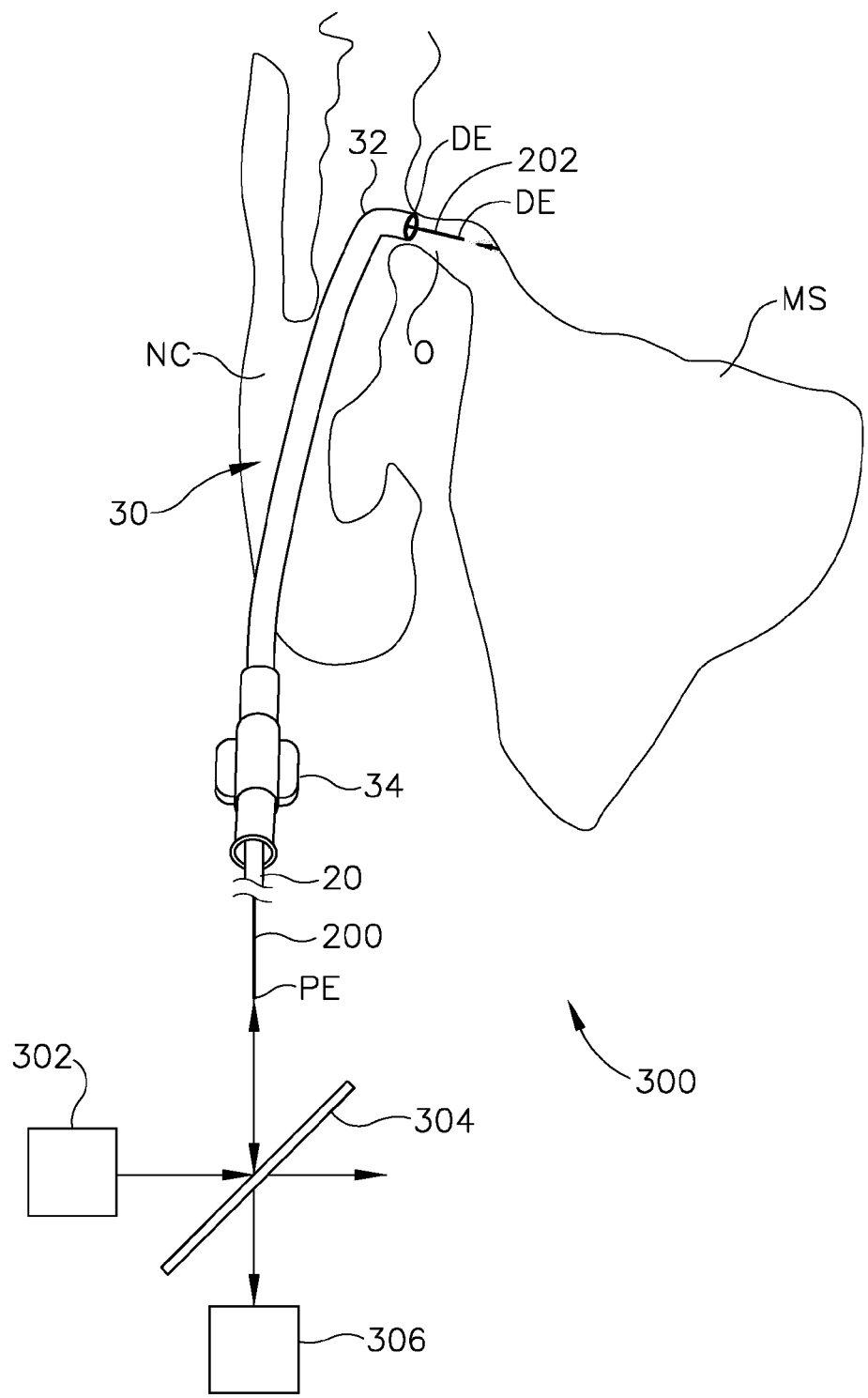
FIG. 10B depicts a front view of the guide catheter of FIG. 2B positioned adjacent an ostium of the maxillary sinus, with the illuminating guidewire of FIG. 8 translated distally relative to the guide catheter, and with the illuminating guidewire projecting light into a superior lateral region of the maxillary sinus.

For instance, based upon characteristics of the reflected light (e.g., intensity, color, etc.), detector (306) may be operable to indicate a distance between the distal end (DE) of guidewire (200) and the anatomical structure(s) that surrounds the distal end (DE) of guidewire (200) as well as the color of such anatomical structure(s). In addition, detector (306), based upon quantitative optical spectroscopy, optical coherence tomography, and/or other optical processing techniques, may indicate a distance between the distal end (DE) of guidewire (200) and the anatomical structure(s) that surround the distal end (DE) of guidewire (200) as wells as the type and/or pathology of anatomical structure(s) that surrounds the distal end (DE) of guidewire (200). For instance, as shown in FIG. 10B, as the distal end (DE) of guidewire (200) is advanced toward a wall of the maxillary sinus (MS), the intensity of light reflected toward the distal end (DE) of guidewire (200) increases, thus indicating that the distal end (DE) of guidewire (200) is approaching an anatomical structure. Again, detector (306) and/or components that are coupled with detector (306) may be configured to provide visual, audible, and/or tactile feedback to an operator based on such information.

Figure 10C:
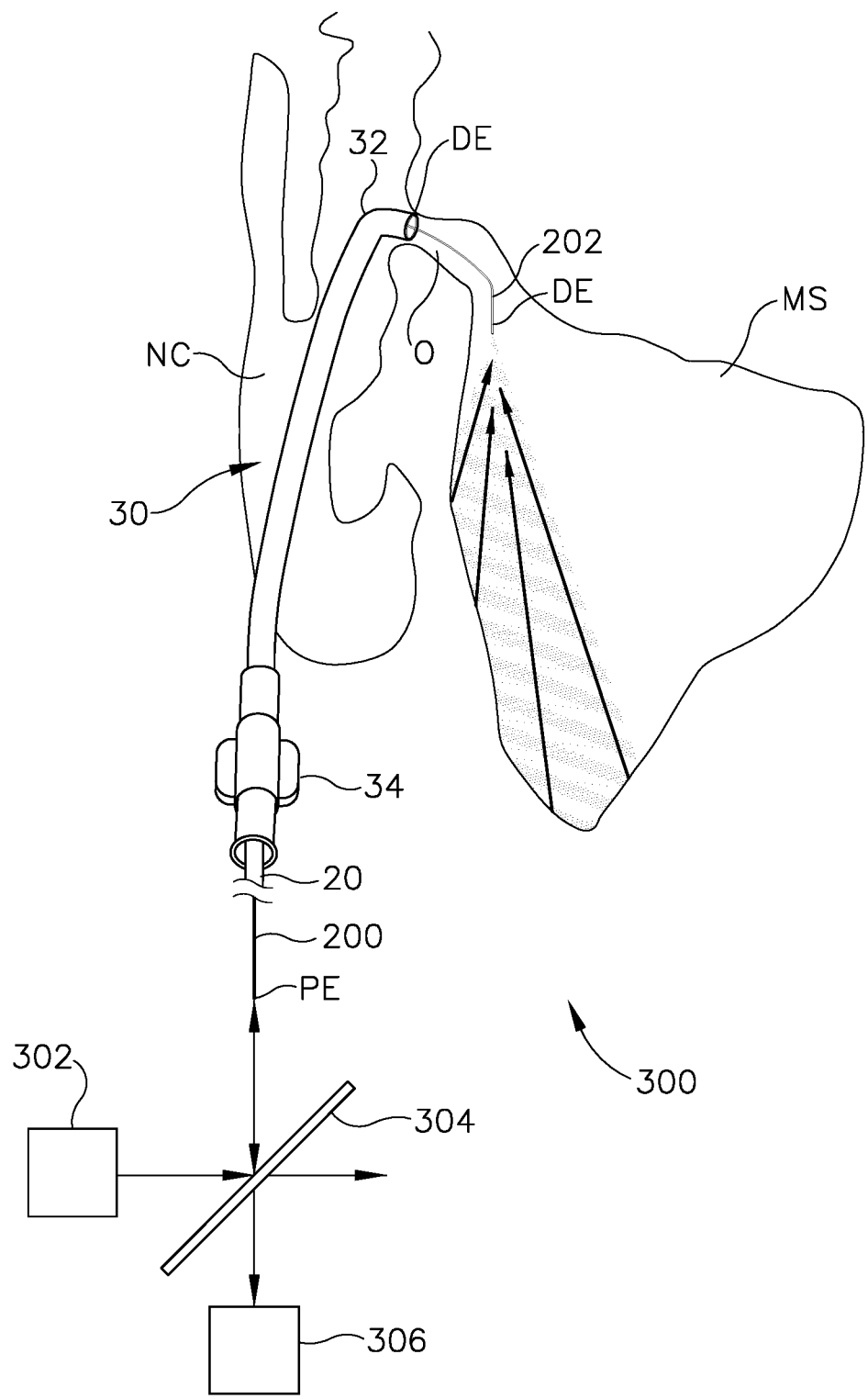
FIG. 10C depicts a front view of the guide catheter of FIG. 2B positioned adjacent an ostium of the maxillary sinus, with the illuminating guidewire of FIG. 8 translated further distally relative to the guide catheter and into the maxillary sinus, with the illuminating guide wire rotated to a first rotational position, and with the illuminating guidewire projecting light into an inferior medial region of the maxillary sinus.
Figure 10D:
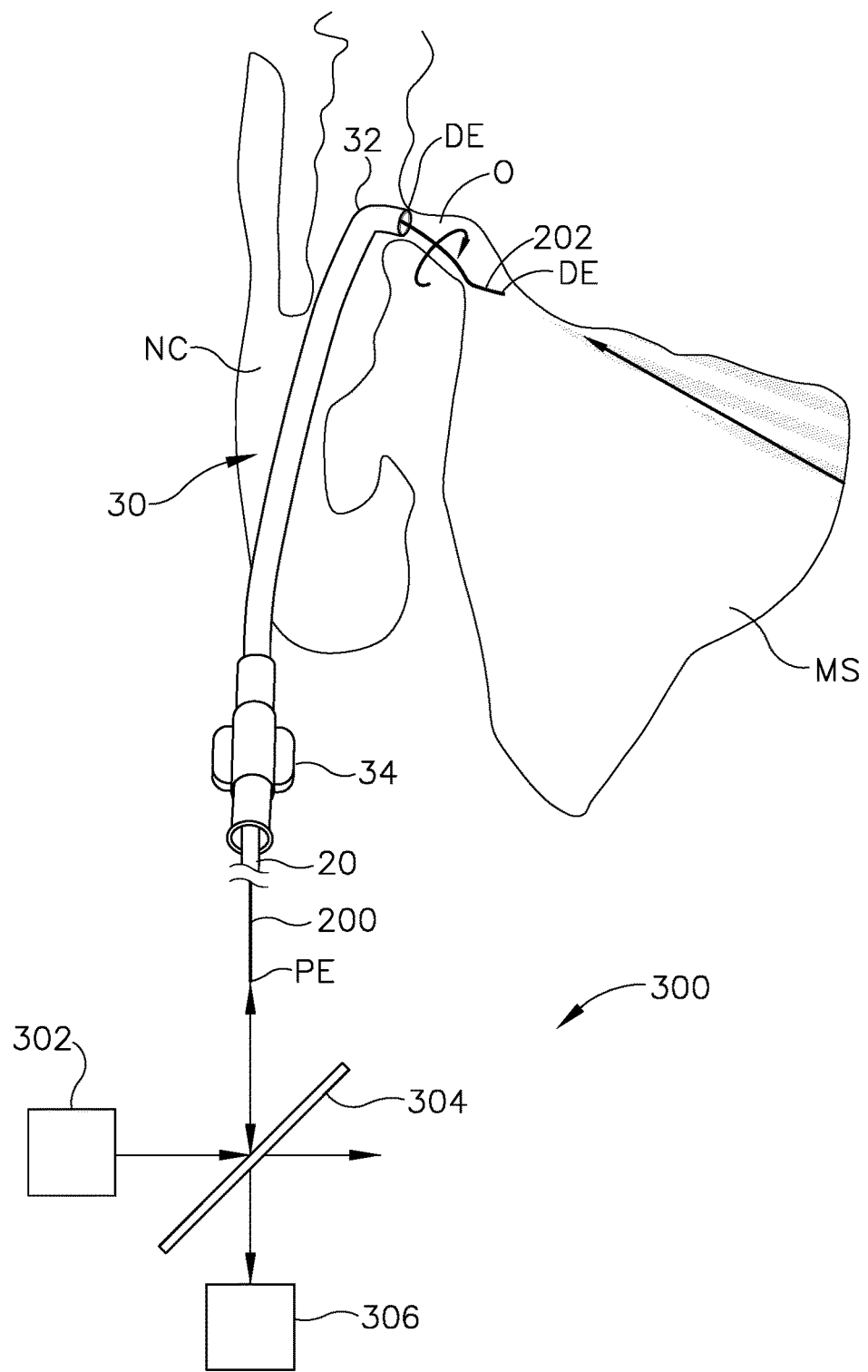
FIG. 10D depicts a front view of the guide catheter of FIG. 2B positioned adjacent an ostium of the maxillary sinus, with the illuminating guide wire of FIG. 8 rotated to a second rotational position, and with the illuminating guidewire projecting light into a superior lateral region of the maxillary sinus.
Figure 10E:
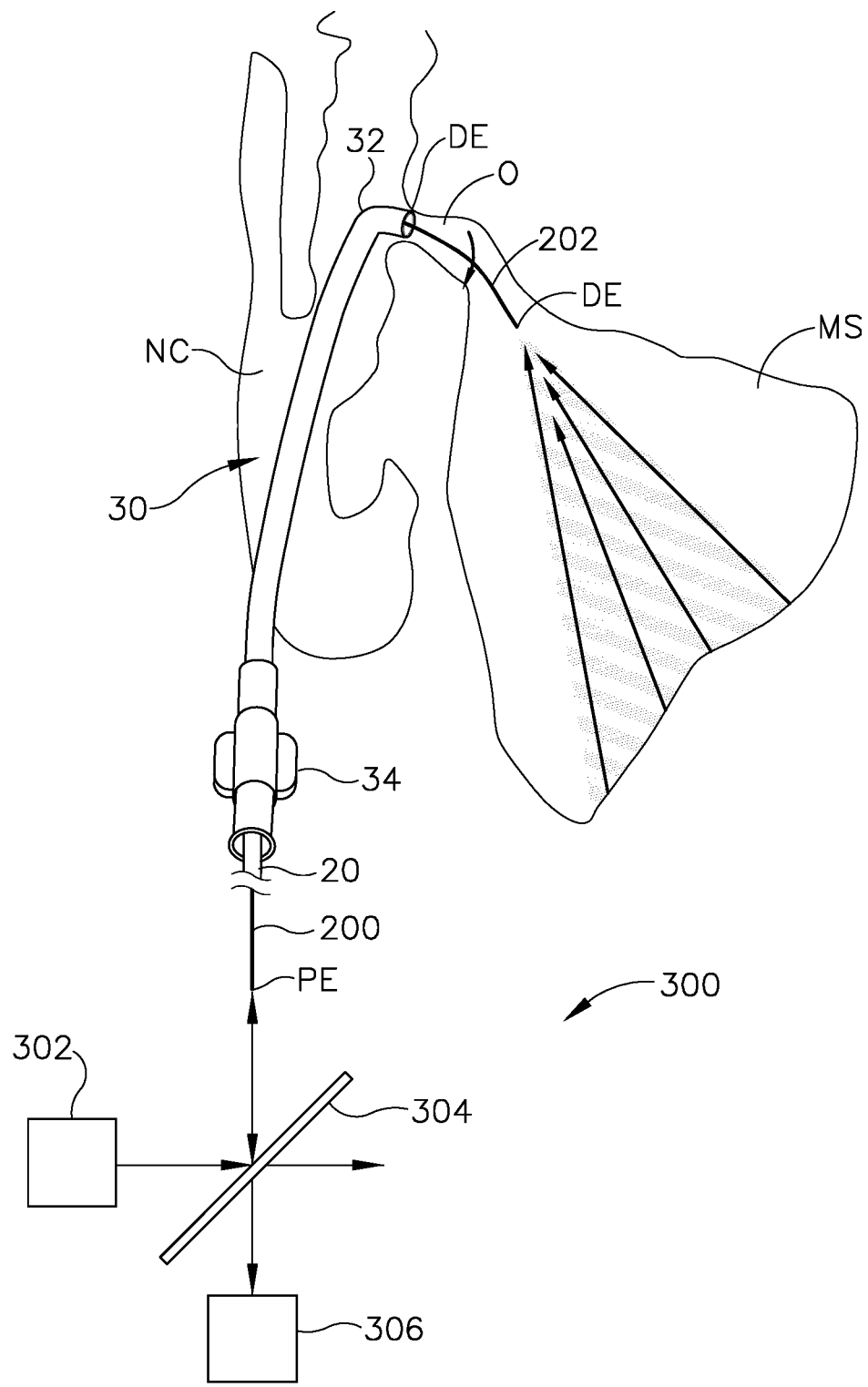
FIG. 10E depicts a front view of the guide catheter of FIG. 2B positioned adjacent an ostium of the maxillary sinus, with the illuminating guide wire of FIG. 8 rotated to a third rotational position, and with the illuminating guidewire projecting light into an inferior region of the maxillary sinus.
Figure 10F:
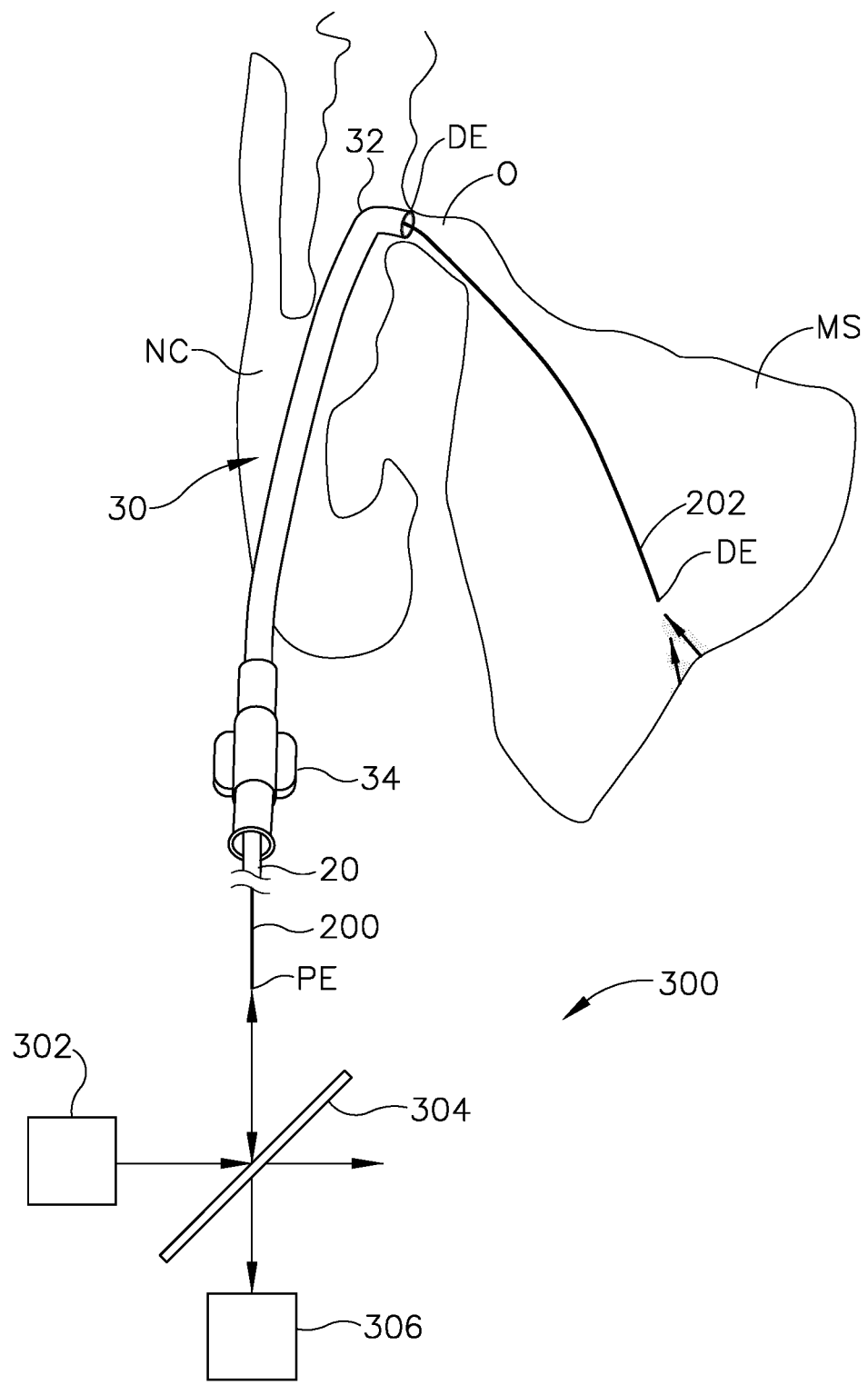
FIG. 10F depicts a front view of the guide catheter of FIG. 2B positioned adjacent an ostium of the maxillary sinus, with the illuminating guidewire of FIG. 8 translated further distally relative to the guide catheter into the maxillary sinus, and with the illuminating guidewire projecting light into an inferior region of the maxillary sinus.

As shown in FIG. 10C, the operator may advance guidewire (200) distally through guide catheter (30) such that a distal portion of the guidewire (200) passes through the ostium (O) of the maxillary sinus (MS) and into the cavity of the maxillary sinus (MS). As this occurs, guidewire (200) is constantly projecting light from its distal end (DE) so as to provide continuous feedback to the operator. As shown in FIGS. 10C-10E, as guidewire (200) is rotated within the maxillary sinus (MS), bent distal portion (202) causes light from the distal end (DE) of guidewire (200) to be projected over a substantial portion of the maxillary sinus (MS). As such rotation occurs, the operator is able to receive feedback concerning the internal shape of the maxillary sinus (MS) such that the operator can determine along which path to translate guidewire (200) as shown in FIG. 10F.

In the foregoing example, detector (306) is operable to determine and/or indicate the presence and characteristics of reflected light to thereby determine and/or indicate the presence of anatomical structure(s) that are distal to distal end (DE) of guidewire (200). Based on signals from detector (306), detector (306) and/or components that are coupled with detector (306) may further provide real-time feedback to the operator concerning the position of guidewire (200) and/or the anatomical structure(s) that are distal to distal end (DE) of guidewire (200). In addition to being capable of determining the distance between distal end (DE) of guidewire (200) and anatomical structures, the system may further be configured to determine the character of tissue based on reflected light that is received by detector (306). By way of example only, detector (306) and/or components that are coupled with detector (306) may process characteristics of the reflected light such as wavelength, etc.; and may interpret tissue conditions based on such characteristics for the reflected light. For instance, the reflected light may indicate tissue conditions such as density, swelling, infection, and/or various other conditions. Various suitable tissue conditions that may be identified based on the characteristics of light reflected off of the tissue will be apparent to those of ordinary skill in the art in view of the teachings herein. Similarly, various ways of processing reflected light to determine such tissue conditions will be apparent to those of ordinary skill in the art in view of the teachings herein.

Once the operator has determined that guidewire (200) is suitably positioned based on optical feedback provided through the reflected light, the operator may advance dilation catheter (20) along guidewire (200) to position dilator (22) in the ostium (O) of the maxillary sinus (MS). The operator may then inflate dilator (22) as described above to dilate the ostium (O). Alternatively, the operator may perform any other desired actions within the maxillary sinus (MS), within the ostium (O), and/or elsewhere. It should be understood that, while the present example is being provided in the context of a maxillary sinus (MS), guidewire (200) may be used in various other procedures. By way of example only, guidewire (200) and variations thereof may be used in or near a Eustachian tube, a larynx, a choana, a sphenoid sinus, one or more ethmoid sinus air cells, the frontal recess, the frontal sinus, other paranasal cavities, and/or other passageways associated with paranasal sinuses. Other suitable ways in which guidewire (200) may be used will be apparent to those of ordinary skill in the art in view of the teachings herein.

B. Exemplary Illuminating Guidewire System with Multiple Optical Fibers

FIG. 11 depicts another exemplary flexible-illuminating guidewire (400) that may be readily incorporated into dilation catheter system (10) in place of guidewire (50). Guidewire (400) of the present example comprises a coil (404) positioned about a core wire (406). A pair of illumination fibers (407, 408) extends along the interior of core wire (406) and terminates in an atraumatic lens (410). Lens (410) is configured to project light when illumination fiber (407) is illuminated by a light source, such that illumination fiber (407) transmits light from the light source to the lens (410). As will be discussed in more detail below, lens (410) is further configured to receive and transmit light to illumination fiber (408) when that light is reflected from beyond the distal end (DE) of guidewire (400).

In the present example, guidewire (400) includes a bent distal portion (402) in accordance with the above discussion of guidewire (200). In some other versions, the distal portion of guidewire (400) is straight. It should also be understood that the distal end (DE) of guidewire (400) may be more flexible than the proximal end (PE) of guidewire (400). Guidewire (400) has a length enabling the distal end (DE) of guidewire (400) to be positioned distal to dilator (22) while the proximal end (PE) of guidewire (400) is positioned proximal to grip (24). Guidewire (400) may include indicia along at least part of its length (e.g., the proximal portion) to provide the operator with visual feedback indicating the depth of insertion of guidewire (400) relative to dilation catheter (20). By way of example only, guidewire (400) may be configured and operable in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (400) is configured similar to the Relieva Luma Sentry™ Sinus Illumination System by Acclarent, Inc. of Menlo Park, Calif. Other suitable forms that guidewire (400) may take will be apparent to those of ordinary skill in the art in view of the teachings herein.

FIGS. 12A-12F show an exemplary illuminating system (500) and an exemplary method for using illuminating system (500) with guidewire (400) to access the maxillary sinus (MS) of a patient. Illuminating system (500) of the present example comprises a conventional light source (502) and a conventional light detector (506). Light source (502) is optically coupled with illumination fiber (407) while light detector (506) is optically coupled with illumination fiber (408). Light source (502) may comprise any suitable kind of light source (502) and may include various components, including but not limited to a laser, a beam collimator, focusing optics, etc. Light source (502) may be operable to communicate any suitable kind of light, including but not limited to white/visible light, near-infrared light, infrared light, etc. Light detector (506) is configured to receive light that is transmitted through illumination fiber (408). Light detector (506) includes a sensor that is operable to generate electrical signals based on light received by the sensor.

Light detector (506) (and/or one or more components that are coupled with light detector (506)) may further include hardware that is configured to process those generated electrical signals and generate some kind of output that provides feedback to the operator relating to the light received by light detector (506). Such feedback may include audible feedback (e.g., an audible tone, a voice providing spoken words, etc.), visual feedback (e.g., a selectively illuminating LED, a graphical interface providing graphic and/or textual feedback, etc.), and/or tactile feedback (e.g., a feature providing a vibration through a handpiece associated with guide catheter (30), etc.). Various suitable forms that light source (502) and light detector (506) (and associated components) may take will be apparent to those of ordinary skill in the art in view of the teachings herein. Similarly, various suitable forms that operator feedback may take will be apparent to those of ordinary skill in the art in view of the teachings herein. In some instances, it may be desirable to configure detector (506) such that detector (506) is operable to "subtract" any unwanted light from light scattering, reflection, or other optical phenomena so as to improve upon the information indicated by detector (506). Various suitable ways in which such subtraction may be provided will be apparent to those of ordinary skill in the art in view of the teachings herein.

Figure 12A:
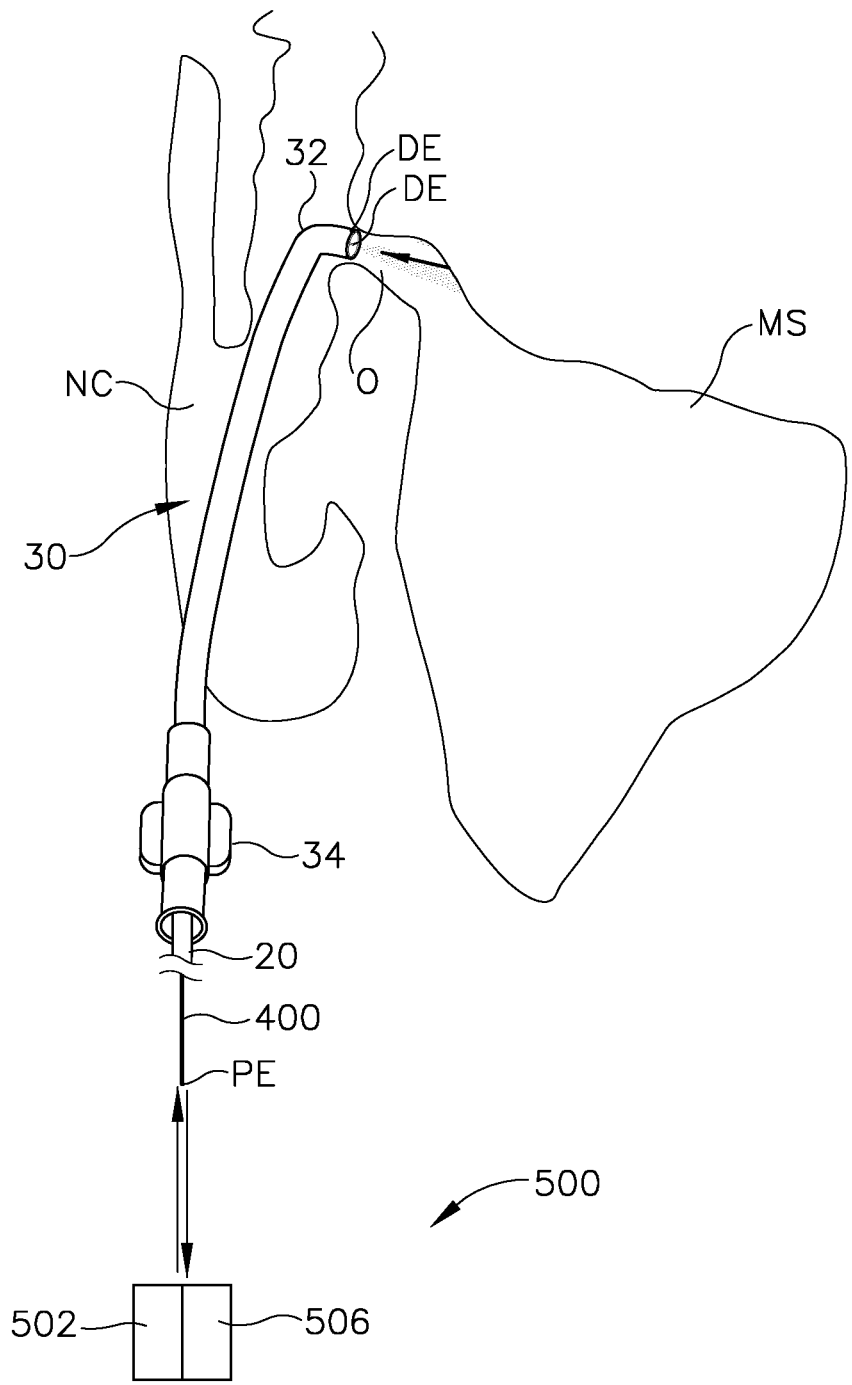
FIG. 12A depicts a front view of the guide catheter of FIG. 2B positioned adjacent an ostium of the maxillary sinus, with the dilation catheter of FIG. 2C and the illuminating guidewire of FIG. 11 positioned therein, and with the illuminating guidewire projecting light through the ostium of the maxillary sinus.

In an exemplary procedure, guide catheter (30) may be inserted transnasally and advanced through the nasal cavity (NC) to a position within or near the ostium (O) of the maxillary sinus (MO) as shown in FIG. 12A. At this stage, the distal end (DE) of guidewire (400) may be positioned adjacent the distal end (DE) of guide catheter (30). At the same time, light source (502) projects light toward illumination fiber (407) of guidewire (400). This light is transmitted through illumination fiber (407) and is emitted from the distal end (DE) of guidewire (400) via lens (410). This emitted light can serve as a source of transilluminating light operable to indicate a position of the distal end (DE) of guidewire (400) by visualization through the anatomical structure(s) that surrounds the distal end (DE) of guidewire (400). Further, the anatomical structure(s) that surrounds the distal end (DE) of guidewire (400) may reflect at least a portion of this emitted light back toward the distal end (DE) of guidewire (400). This reflected light enters illumination fiber (408) via lens (410). The reflected light is then transmitted proximally through illumination fiber (408) and is emitted from the proximal end (PE) of guidewire (400) toward detector (506). Detector (506) is then operable to determine and/or indicate the presence and characteristics of reflected light to thereby determine and/or indicate the presence of anatomical structure(s) that are distal to distal end (DE) of guidewire (400). As noted above, based on the detected light that is reflected back from anatomical structure(s) that are distal to distal end (DE) of guidewire (400), detector (506) and/or components that are coupled with detector (506) may further provide real-time feedback to the operator concerning the position of guidewire (400) and/or the anatomical structure(s) that are distal to distal end (DE) of guidewire (400).

Figure 12B:
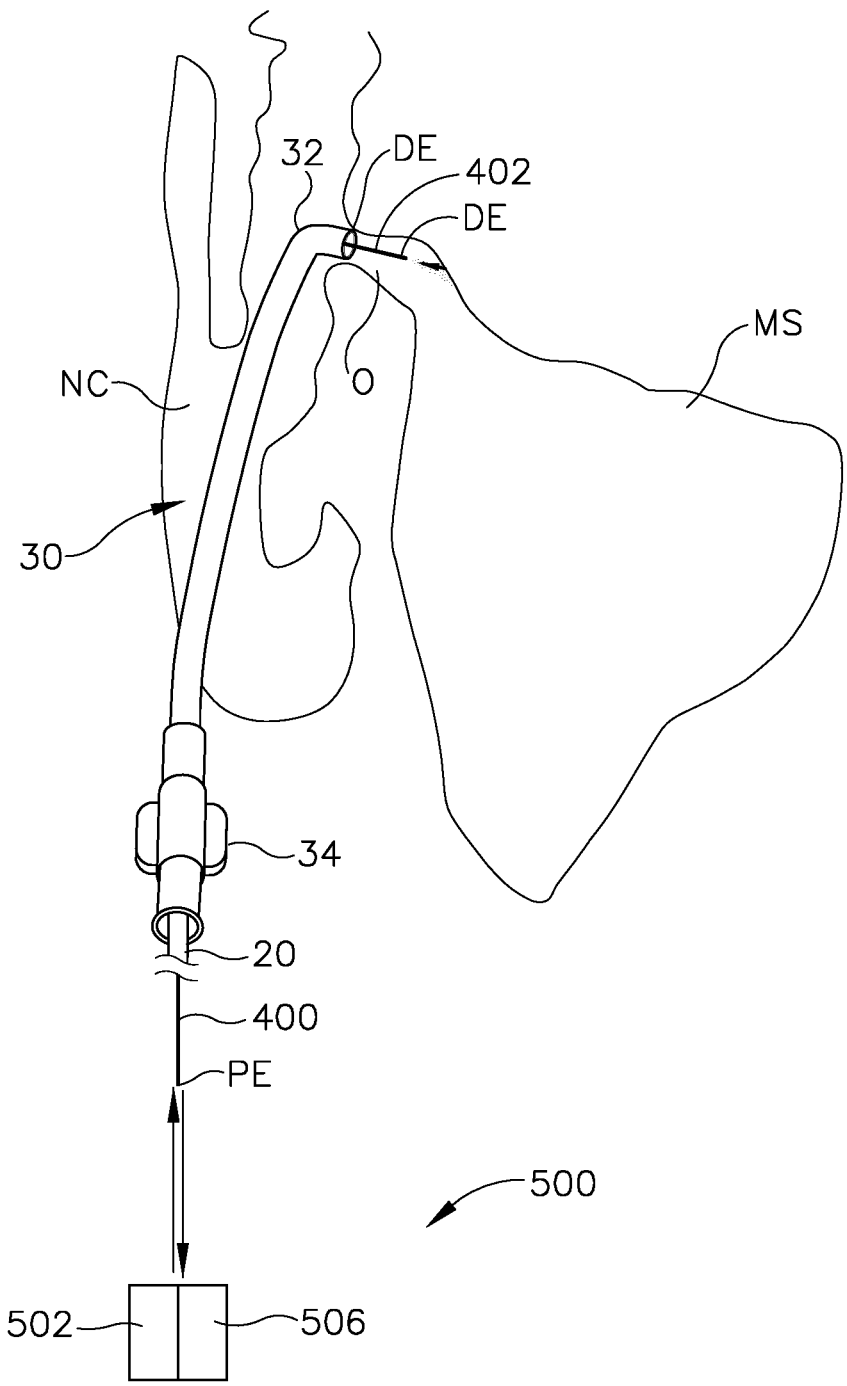
FIG. 12B depicts a front view of the guide catheter of FIG. 2B positioned adjacent an ostium of the maxillary sinus, with the illuminating guidewire of FIG. 11 translated distally relative to the guide catheter, and with the illuminating guidewire projecting light into a superior lateral region of the maxillary sinus.

For instance, based upon characteristics of the reflected light (e.g., intensity, color, etc.), detector (506) may be operable to indicate a distance between the distal end (DE) of guidewire (400) and the anatomical structure(s) that surrounds the distal end (DE) of guidewire (400) as well as the color of such anatomical structure(s). In addition, detector (506), based upon quantitative optical spectroscopy, optical coherence tomography, and/or other optical processing techniques, may indicate a distance between the distal end (DE) of guidewire (400) and the anatomical structure(s) that surround the distal end (DE) of guidewire (200) as wells as the type and/or pathology of anatomical structure(s) that surrounds the distal end (DE) of guidewire (400). For instance, as shown in FIG. 12B, as the distal end (DE) of guidewire (400) is advanced toward a wall of the maxillary sinus (MS), the intensity of light reflected toward the distal end (DE) of guidewire (400) increases, thus indicating that the distal end (DE) of guidewire (400) is approaching an anatomical structure. Again, detector (506) and/or components that are coupled with detector (506) may be configured to provide visual, audible, and/or tactile feedback to an operator based on such information.

Figure 12C:
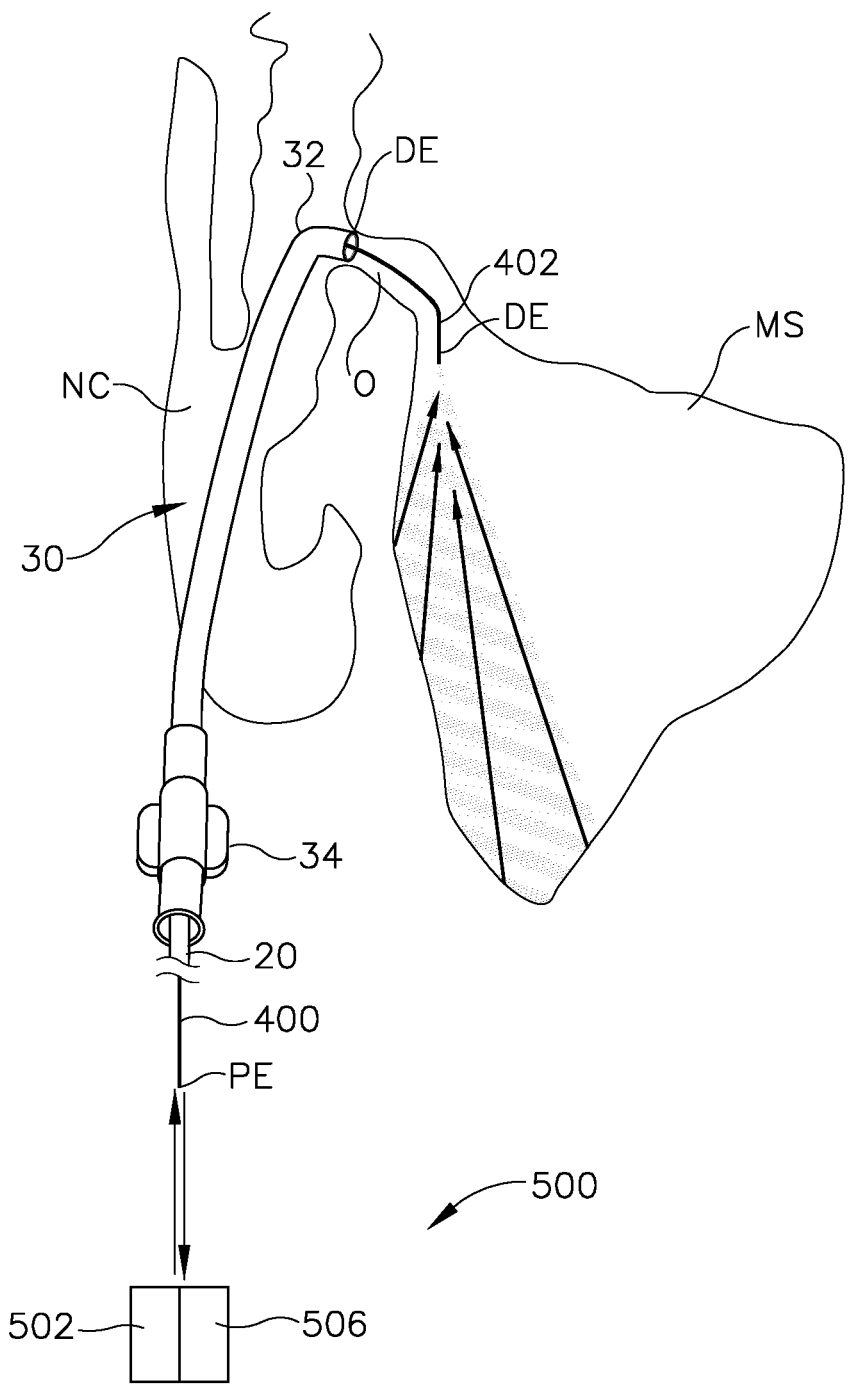
FIG. 12C depicts a front view of the guide catheter of FIG. 2B positioned adjacent an ostium of the maxillary sinus, with the illuminating guidewire of FIG. 11 translated further distally relative to the guide catheter and into the maxillary sinus, with the illuminating guide wire rotated to a first rotational position, and with the illuminating guidewire projecting light into an inferior medial region of the maxillary sinus.
Figure 12D:
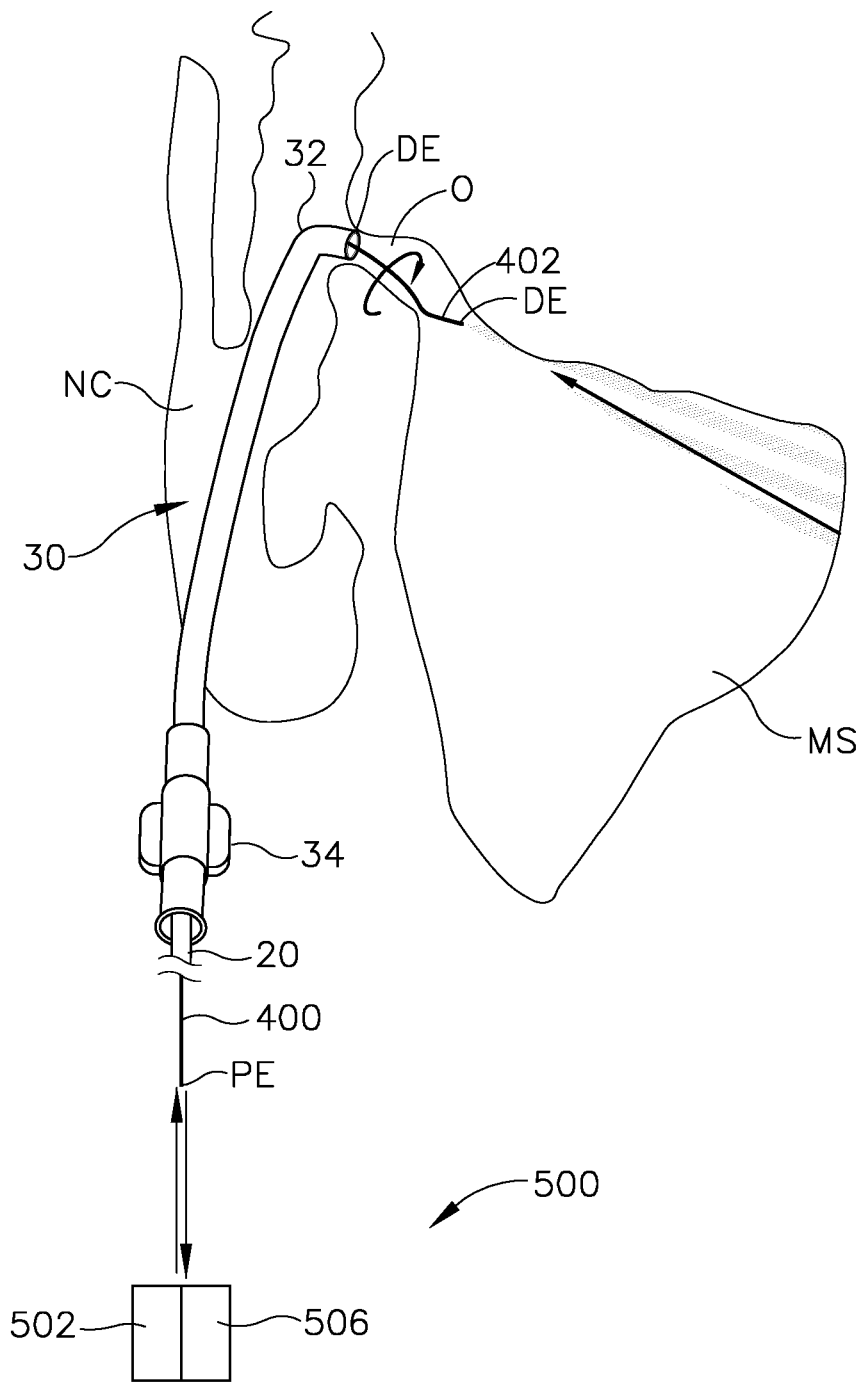
FIG. 12D depicts a front view of the guide catheter of FIG. 2B positioned adjacent an ostium of the maxillary sinus, with the illuminating guide wire of FIG. 11 rotated to a second rotational position, and with the illuminating guidewire projecting light into a superior lateral region of the maxillary sinus.
Figure 12E:
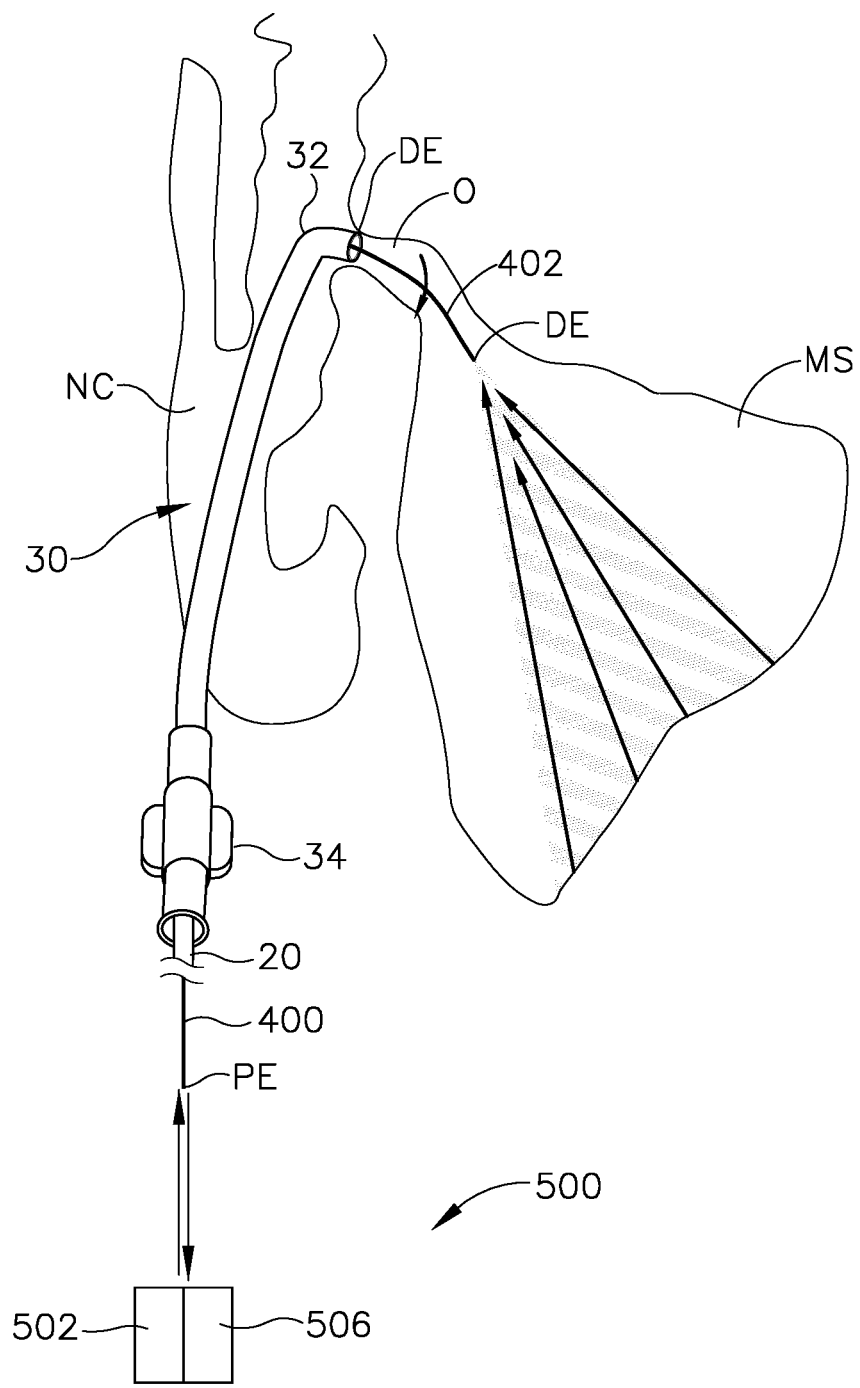
FIG. 12E depicts a front view of the guide catheter of FIG. 2B positioned adjacent an ostium of the maxillary sinus, with the illuminating guide wire of FIG. 11 rotated to a third rotational position, and with the illuminating guidewire projecting light into an inferior region of the maxillary sinus.
Figure 12F:
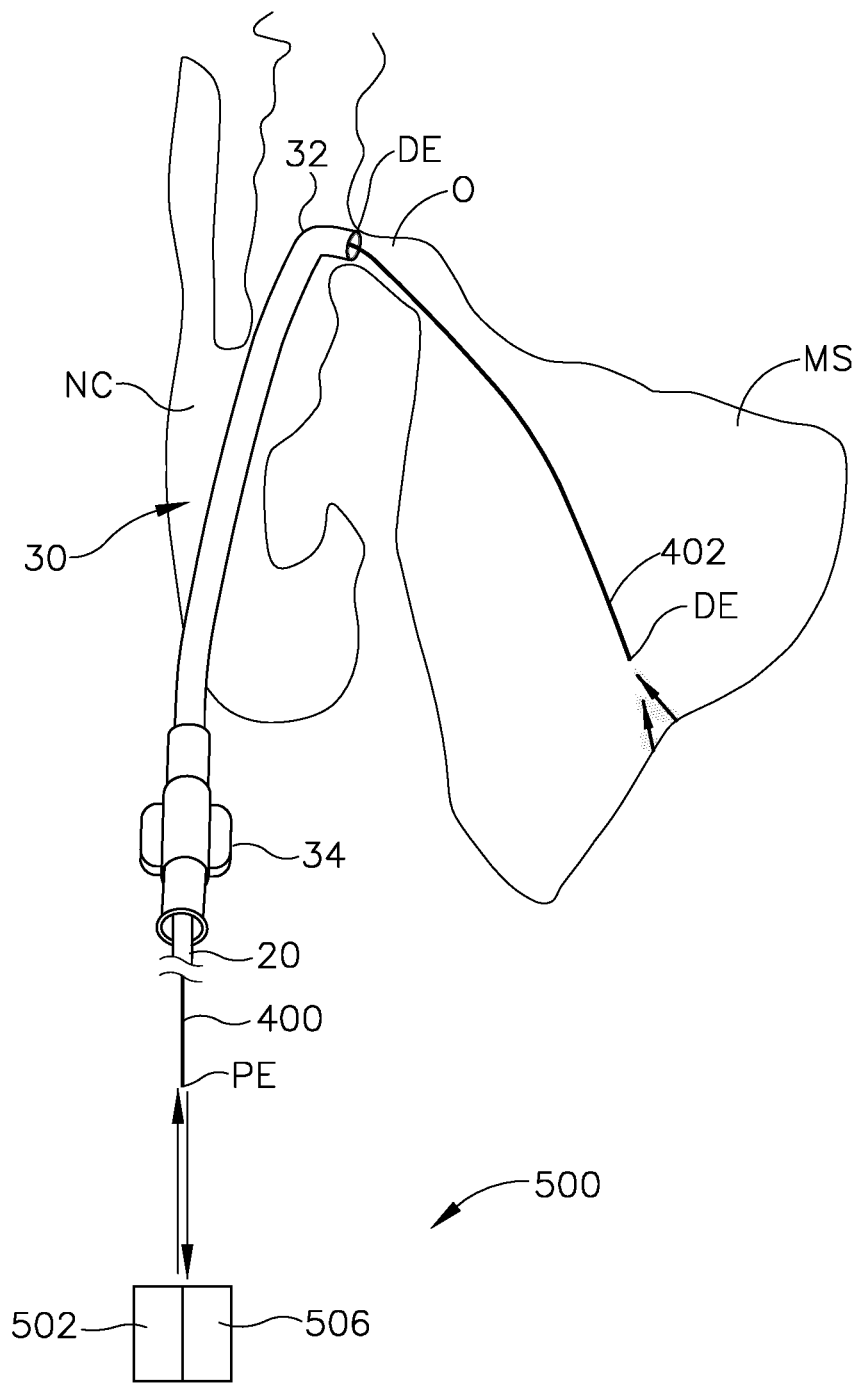
FIG. 12F depicts a front view of the guide catheter of FIG. 2B positioned adjacent an ostium of the maxillary sinus, with the illuminating guidewire of FIG. 11 translated further distally relative to the guide catheter into the maxillary sinus, and with the illuminating guidewire projecting light into an inferior region of the maxillary sinus.

As shown in FIG. 12C, the operator may advance guidewire (400) distally through guide catheter (30) such that a distal portion of the guidewire (400) passes through the ostium (O) of the maxillary sinus (MS) and into the cavity of the maxillary sinus (MS). As this occurs, guidewire (400) is constantly projecting light from its distal end (DE) so as to provide continuous feedback to the operator. As shown in FIGS. 12C-12E, as guidewire (400) is rotated within the maxillary sinus (MS), bent distal portion (402) causes light from the distal end (DE) of guidewire (400) to be projected over a substantial portion of the maxillary sinus (MS). As such rotation occurs, the operator is able to receive feedback concerning the internal shape of the maxillary sinus (MS) such that the operator can determine along which path to translate guidewire (400) as shown in FIG. 12F.

Once the operator has determined that guidewire (400) is suitably positioned based on optical feedback provided through the reflected light, the operator may advance dilation catheter (20) along guidewire (400) to position dilator (22) in the ostium (O) of the maxillary sinus (MS). The operator may then inflate dilator (22) as described above to dilate the ostium (O). Alternatively, the operator may perform any other desired actions within the maxillary sinus (MS), within the ostium (O), and/or elsewhere. It should be understood that, while the present example is being provided in the context of a maxillary sinus (MS), guidewire (400) may be used in various other procedures. By way of example only, guidewire (400) and variations thereof may be used in or near a Eustachian tube, a larynx, a choana, a sphenoid sinus, one or more ethmoid sinus air cells, the frontal recess, the frontal sinus, other paranasal cavities, and/or other passageways associated with paranasal sinuses. Other suitable ways in which guidewire (400) may be used will be apparent to those of ordinary skill in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A guide system comprising: (a) a guide member, wherein the guide member comprises a proximal end and a distal end, wherein the guide member comprises at least one illumination fiber; (b) a light source, wherein the light source is operable to project light to the proximal end of the guide member, wherein the at least one illumination fiber is operable to distally transmit the light projected by the light source from the proximal end of the guide member to the distal end of the guide member, wherein the distal end of the guide member is operable to project the distally transmitted light, wherein the distal end of the guide member is further operable to receive light projected from the distal end of the guide member and reflected back toward the distal end of the guide member, wherein the at least one illumination fiber is operable to proximally transmit the reflected light from the distal end of the guide member to the proximal end of the guide member; and (c) a detector, wherein the proximal end of the guide member is operable to project the proximally transmitted light toward the detector, wherein the detector is operable to detect the proximally transmitted light.

Example 2

The guide system of Example 1, wherein the distal end of the guide member comprises an atraumatic lens.

Example 3

The guide system of any one or more of Examples 1 through 2, wherein the distal end of the guide member comprises a preformed bend.

Example 4

The guide system of any one or more of Examples 1 through 2, further comprising a beam splitter, wherein the beam splitter is interposed between the light source and the at least one illumination fiber.

Example 5

The guide system of Example 4, wherein the beam splitter is operable to redirect the light projected by the light source toward the proximal end of the guide member.

Example 6

The guide system of any one or more of Examples 4 through 5, wherein the beam splitter is interposed between the at least one illumination fiber and the detector, wherein the beam splitter is operable to transmit the light projected by the proximal end of the guide member toward the detector.

Example 7

The guide system of any one or more of Examples 1 through 6, wherein the at least one illumination fiber consists of a single illumination fiber, wherein the single illumination fiber is operable to both: (i) distally transmit the light projected by the light source from the proximal end of the guide member to the distal end of the guide member, and (ii) proximally transmit the reflected light from the distal end of the guide member to the proximal end of the guide member.

Example 8

The guide system of any one or more of Examples 1 through 7, wherein the guide member comprises a guidewire.

Example 9

The guide system any one or more of Examples 1 through 6 and 8, wherein the at least one illumination fiber comprises a first illumination fiber and a second illumination fiber, wherein the first illumination fiber is operable to distally transmit the light projected by the light source from the proximal end of the guide member to the distal end of the guide member.

Example 10

The guide system of Example 9, wherein the second illumination fiber is operable to proximally transmit the reflected light from the distal end of the guide member to the proximal end of the guide member.

Example 11

The guide system of any one or more of Examples 1 through 10, wherein the detector is further operable to determine the presence of an anatomical structure based upon the reflected light.

Example 12

The guide system of Example 11, wherein the detector is further operable to determine the distance between the anatomical structure and the distal end of the guide member based upon the reflected light.

Example 13

The guide system of any one or more of Examples 11 through 12, wherein the detector is further operable to determine the color of the anatomical structure based upon the reflected light.

Example 14

The guide system of any one or more of Examples 11 through 13, wherein the detector is further operable to determine the type of the anatomical structure based upon the reflected light.

Example 15

The guide system of any one or more of Examples 11 through 14, wherein the detector is further operable to determine the pathology of the anatomical structure based upon the reflected light.

Example 16

The guide system of any one or more of Examples 1 through 15, wherein the detector is further operable to provide indications and/or feedback to an operator based upon the reflected light.

Example 17

The guide system of any one or more of Examples 1 through 16, wherein the system further comprises a guide catheter, wherein the guide member is configured to pass through the guide catheter.

Example 18

The guide system of any one or more of Examples 1 through 17, wherein the system further comprises a balloon dilation catheter, wherein the balloon dilation catheter is configured to slide along the guide member.

Example 19

A guide member positioning system comprising: (a) a guide member, wherein the guide member comprises a proximal end and a distal end, wherein the guide member comprises at least one illumination fiber, wherein the at least one illumination fiber is operable to transmit light from the proximal end to the distal end; (b) a light source, wherein the light source is operable to project light to the proximal end of the guide member; (c) a beam splitter, wherein the beam splitter is operable to redirect the light projected by the light source toward the proximal end of the guide member, wherein the at least one illumination fiber is operable to distally transmit the light redirected by the beam splitter from the proximal end of the guide member to the distal end of the guide member, wherein the distal end of the guide member is operable to project the distally transmitted light, wherein the distal end of the guide member is further operable to receive light projected from the distal end of the guide member and reflected back toward the distal end of the guide member, wherein the at least one illumination fiber is operable to proximally transmit the reflected light from the distal end of the guide member to the proximal end of the guide member, wherein the proximal end of the guide member is operable to project the proximally transmitted light toward the beam splitter; and (d) a detector, wherein the beam splitter is operable to transmit the light projected by the proximal end of the guide member toward the detector, wherein the detector is operable to detect the proximally transmitted light.

Example 20

A guide member positioning system comprising: (a) a guide member, wherein the guide member comprises a proximal end and a distal end, wherein the guide member comprises a first illumination fiber and a second illumination fiber; (b) a light source, wherein the light source is operable to project light to the first illumination fiber, wherein the first illumination fiber is operable to distally transmit the light projected by the light source from the proximal end of the guide member to the distal end of the guide member, wherein the distal end of the guide member is further operable to receive light projected from the distal end of the guide member and reflected back toward the distal end of the guide member, wherein the second illumination fiber is operable to proximally transmit the reflected light from the distal end of the guide member to the proximal end of the guide member; and (c) a detector, wherein the proximal end of the guide member is operable to project the proximally transmitted light toward the detector, wherein the detector is operable to detect the proximally transmitted light.

VI. Miscellaneous

While terms such as "light" and "light source" are used herein, it is contemplated that these terms include more than just visible light and sources of visible light. By way of example only, it is contemplated that the present teachings may be applied using infrared light, ultraviolet light, and other light that is not necessarily visible to the naked human eye. Therefore, the term "light" should be read to include non-visible light in addition to including non-visible light. Likewise, the term "light source' should be read to include sources of visible light in addition to sources of non-visible light.

While the examples herein provide light through a guidewire (200, 400), it should be understood that the teachings herein may also be readily applied to various other kinds of guide members, including but not limited to guide catheters, guide fibers, guide rods, etc. Various other suitable components that may be used to project light and receive reflected light will be apparent to those of ordinary skill in the art in view of the teachings herein.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A guide system comprising:
    (a) a guide member, wherein the guide member comprises a proximal end and a distal end, wherein the guide member comprises at least one illumination fiber;
    (b) a light source, wherein the light source is operable to project light to the proximal end of the guide member, wherein the at least one illumination fiber is operable to distally transmit the light projected by the light source from the proximal end of the guide member to the distal end of the guide member, wherein the distal end of the guide member is operable to project the distally transmitted light, wherein the distal end of the guide member is further operable to receive light projected from the distal end of the guide member and reflected back toward the distal end of the guide member, wherein the at least one illumination fiber is operable to proximally transmit the reflected light from the distal end of the guide member to the proximal end of the guide member;
    (c) a detector, wherein the proximal end of the guide member is operable to project the proximally transmitted light toward the detector, wherein the detector is operable to detect the proximally transmitted light;
    (d) a guide catheter, wherein the guide member is configured to slide through the guide catheter; and
    (e) a balloon dilation catheter, wherein the balloon dilation catheter is configured to slide along the guide member.

2. The guide system of claim 1, wherein the distal end of the guide member comprises an atraumatic lens.

3. The guide system of claim 1, wherein the distal end of the guide member comprises a preformed bend.

4. The guide system of claim 1, further comprising a beam splitter, wherein the beam splitter is interposed between the light source and the at least one illumination fiber.

5. The guide system of claim 4, wherein the beam splitter is operable to redirect the light projected by the light source toward the proximal end of the guide member.

6. The guide system of claim 4, wherein the beam splitter is interposed between the at least one illumination fiber and the detector, wherein the beam splitter is operable to transmit the light projected by the proximal end of the guide member toward the detector.

7. The guide system of claim 1, wherein the at least one illumination fiber consists of a single illumination fiber, wherein the single illumination fiber is operable to both:
    (i) distally transmit the light projected by the light source from the proximal end of the guide member to the distal end of the guide member, and
    (ii) proximally transmit the reflected light from the distal end of the guide member to the proximal end of the guide member.

8. The guide system of claim 1, wherein the guide member comprises a guidewire.

9. The guide system of claim 8, wherein the at least one illumination fiber comprises a first illumination fiber and a second illumination fiber, wherein the first illumination fiber is operable to distally transmit the light projected by the light source from the proximal end of the guide member to the distal end of the guide member.

10. The guide system of claim 9, wherein the second illumination fiber is operable to proximally transmit the reflected light from the distal end of the guide member to the proximal end of the guide member.

11. The guide system of claim 1, wherein the detector is further operable to determine the presence of an anatomical structure based upon the reflected light.

12. The guide system of claim 11, wherein the detector is further operable to determine the distance between the anatomical structure and the distal end of the guide member based upon the reflected light.

13. The guide system of claim 11, wherein the detector is further operable to determine the color of the anatomical structure based upon the reflected light.

14. The guide system of claim 11, wherein the detector is further operable to determine the type of the anatomical structure based upon the reflected light.

15. The guide system of claim 11, wherein the detector is further operable to determine the pathology of the anatomical structure based upon the reflected light.

16. The guide system of claim 1, wherein the detector is further operable to provide indications and/or feedback to an operator based upon the reflected light.

17. The guide system of claim 1, wherein the guide catheter is configured to slidably receive the balloon dilation catheter with the guide member positioned in the balloon dilation catheter.

18. A guide member positioning system comprising:
   (a) a guide member, wherein the guide member comprises a proximal end and a distal end, wherein the guide member comprises at least one illumination fiber, wherein the at least one illumination fiber is operable to transmit light from the proximal end to the distal end;
   (b) a light source, wherein the light source is operable to project light to the proximal end of the guide member;
   (c) a beam splitter, wherein the beam splitter is operable to redirect the light projected by the light source toward the proximal end of the guide member, wherein the at least one illumination fiber is operable to distally transmit the light redirected by the beam splitter from the proximal end of the guide member to the distal end of the guide member, wherein the distal end of the guide member is operable to project the distally transmitted light, wherein the distal end of the guide member is further operable to receive light projected from the distal end of the guide member and reflected back toward the distal end of the guide member, wherein the at least one illumination fiber is operable to proximally transmit the reflected light from the distal end of the guide member to the proximal end of the guide member, wherein the proximal end of the guide member is operable to project the proximally transmitted light toward the beam splitter;
   (d) a detector, wherein the beam splitter is operable to transmit the light projected by the proximal end of the guide member toward the detector, wherein the detector is operable to detect the proximally transmitted light; and
   (e) a dilation catheter including:
      (i) a dilator,
      (ii) a first lumen in fluid communication with the dilator, and
      (iii) a second lumen, wherein the guide member is slidably disposed in the second lumen.

19. A guide member positioning system comprising:
   (a) a guide member, wherein the guide member comprises a proximal end and a distal end, wherein the guide member comprises a first illumination fiber and a second illumination fiber;
   (b) a light source, wherein the light source is operable to project light to the first illumination fiber, wherein the first illumination fiber is operable to distally transmit the light projected by the light source from the proximal end of the guide member to the distal end of the guide member, wherein the distal end of the guide member is further operable to receive light projected from the distal end of the guide member and reflected back toward the distal end of the guide member, wherein the second illumination fiber is operable to proximally transmit the reflected light from the distal end of the guide member to the proximal end of the guide member;
   (c) a detector, wherein the proximal end of the guide member is operable to project the proximally transmitted light toward the detector, wherein the detector is operable to detect the proximally transmitted light, wherein the detector is operable to filter out scattered, reflected or other peripheral light external of the light transmitted from the proximal end;
   (d) a guide catheter, wherein the guide member is configured to rotate within the guide catheter; and
   (e) a dilation catheter, wherein the dilation catheter is configured to translate along the guide member.

20. The guide system of claim 17, wherein the balloon dilation catheter includes a dilator configured to be selectively inflated and deflated.

* * * * *